(12) United States Patent
Harari et al.

(10) Patent No.: US 6,328,744 B1
(45) Date of Patent: Dec. 11, 2001

(54) BONE SUTURING DEVICE

(75) Inventors: Boaz Harari, Haifa; Mordechay Beyar, Caesarea; Oren Globerman, Kfar-Shmaryahu, all of (IL)

(73) Assignee: American Medical Systems, Inc., Minnetonka, MN (US)

( * ) Notice: Subject to any disclaimer, the term of this patent is extended or adjusted under 35 U.S.C. 154(b) by 0 days.

(21) Appl. No.: 09/476,682

(22) Filed: Dec. 30, 1999

(30) Foreign Application Priority Data

Jun. 4, 1999 (IL) ........................................................ 130307

(51) Int. Cl.[7] .................................................... A61B 17/56
(52) U.S. Cl. .............................. 606/80; 606/96; 606/180; 408/241 R
(58) Field of Search ................................. 606/80, 79, 81, 606/86, 87, 96, 97, 103, 180, 167; 408/241 R, 127, 136, 146; 81/177.6; 175/61.75, 73, 74

(56) References Cited

U.S. PATENT DOCUMENTS

| | | | |
|---|---|---|---|
| 4,312,337 | * | 1/1982 | Donohue ................................ 606/80 |
| 4,345,601 | * | 8/1982 | Fukuda .................................. 606/80 |
| 4,935,027 | | 6/1990 | Yoon . |
| 4,941,466 | | 7/1990 | Romano . |
| 5,002,546 | | 3/1991 | Romano . |
| 5,250,055 | | 10/1993 | Moore et al. . |
| 5,312,403 | | 5/1994 | Frigg . |
| 5,330,479 | | 7/1994 | Whitmore . |
| 5,368,596 | | 11/1994 | Burkhart . |
| 5,509,918 | * | 4/1996 | Romano ................................ 606/80 |
| 5,520,700 | | 5/1996 | Beyar et al. . |
| 5,527,342 | | 6/1996 | Pietrzak et al. . |
| 5,578,032 | | 11/1996 | Lalonda . |
| 5,779,708 | | 7/1998 | Wu . |

FOREIGN PATENT DOCUMENTS

| | | |
|---|---|---|
| 0 478 949 A1 | 4/1992 | (EP) . |
| WO91/11962 | 8/1991 | (WO) . |
| WO97/47246 * | 12/1997 | (WO) ................................ 606/80 |

OTHER PUBLICATIONS

Marketing material of Boston Scientific Microvasive, entitled "Capio™ *Suture Capturing Device*," with a copyright to Boston Scientific Corporation of 1998.

* cited by examiner

*Primary Examiner*—Pedro Philogene
(74) *Attorney, Agent, or Firm*—James W. Inskeep; Oppenheimer Wolff & Donnelly LLP

(57) ABSTRACT

A bone boring device and method wherein the device includes a hinge, a handle coupled to the hinge, and at least one curved needle with a tip. The needle is rotatably mounted on the hinge such that when the tip is placed against bone and the needle is rotated on the hinge, the needle is urged and advanced into the bone.

36 Claims, 35 Drawing Sheets

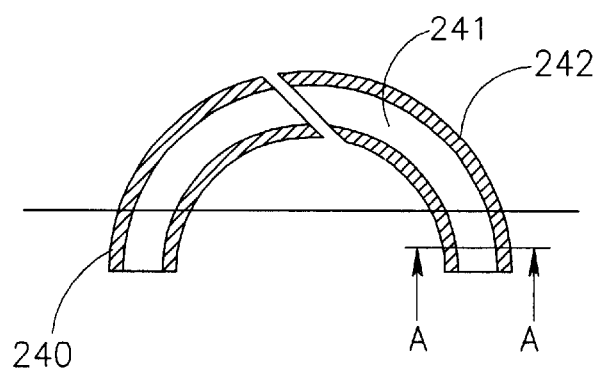 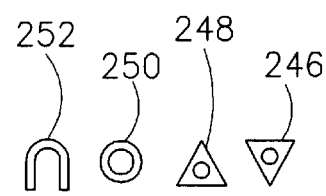
FIG.5A                    FIG.5B
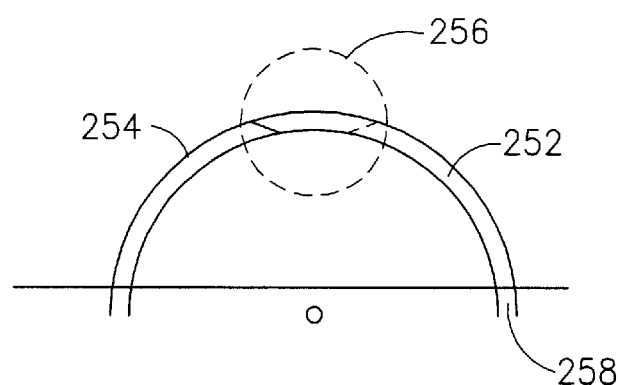 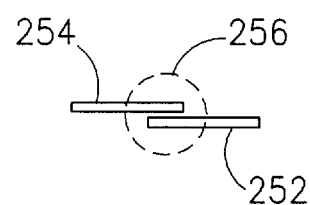
FIG.6A                    FIG.6B
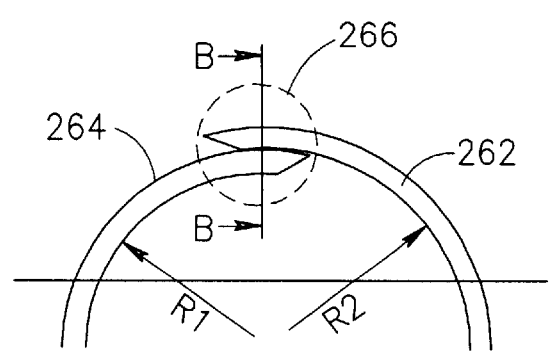 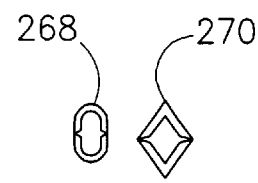
FIG.7A                    FIG.7B

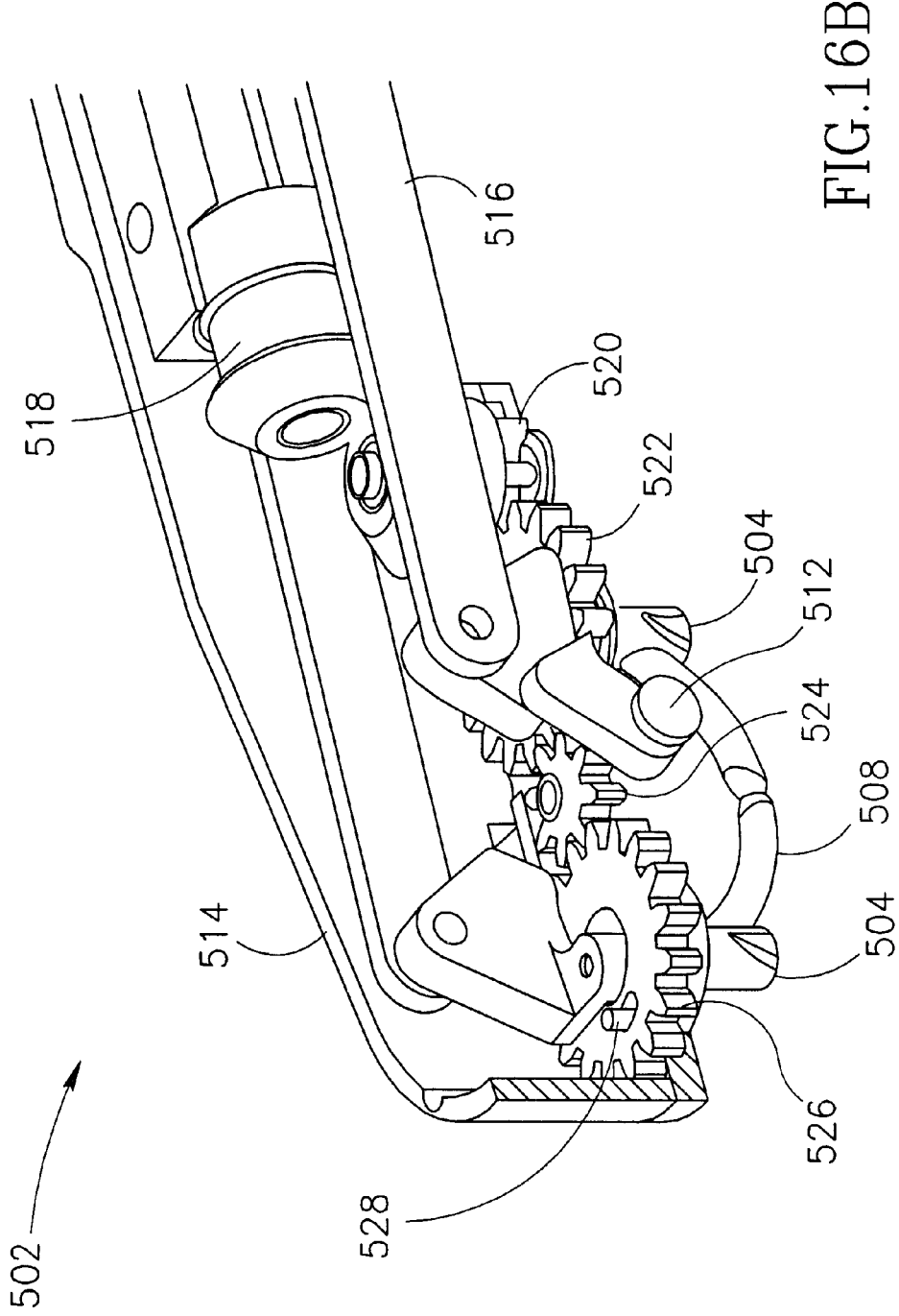

BONE SUTURING DEVICE

FIELD OF THE INVENTION

The present invention relates to forming channels through bones and especially to threading such channels with sutures.

BACKGROUND OF THE INVENTION

Attaching a suture to a bone is a task that is well known in the art of surgery. A common solution is to screw a threaded screw into the bone. However, screwdrivers used to perform this task are often complex and/or expensive. Another solution described for example in U.S. Pat. No. 5,520,700 to Beyar et al., the disclosure of which is incorporated herein by reference, is to insert a threaded bone anchor into the bone. A disadvantage of both this and the previous techniques is that a hard foreign body is left implanted in the body. In general, it is desirable to leave as small an amount as possible of foreign material in the human bone. Additionally, screws and bone anchors typically cause a considerable amount of trauma to the bone, which trauma is undesirable.

PCT publication WO 97/47246, the disclosure of which is incorporated herein by reference, describes a suture insertion device that purports to form channels in a bone for the suture to be tied through the channel. The needles suggested in this PCT publication for forming a curved channel are either curved or are super-elastic needles that are supposed to curve inside the bone. In general, these needles are inserted into the bone at a perpendicular thereto by pushing them along a suitable bore. An alterative method suggested is drilling using a rotary drill, along a curved path. However, it is noted that drills usually damage a large amount of bone.

Biolectron, Inc. provides a device ("CurvTek") which drills along a curved path in a bone, from two ends of the path, using air-pressure powered rotary drill bits,

SUMMARY OF THE INVENTION

An object of some preferred embodiments of the invention is to provide a method of fixing a suture to a bone, while causing a minimum of damage to the bone and/or a minimum of implanted foreign objects, especially a minimum of implanted hard objects.

An aspect of some preferred embodiments of the invention relates to mounting a bone-boring needle on a rotary hinge. One desirable result of this structure is that transfer of power to the tip of the needle is more efficient. Another desirable result is a simpler construction. Another desirable result is obtaining a more controllable and/or known path inside the bone. It should be noted that some or all of these desirable results (and others described herein) might not be achieved in some preferred embodiment of the invention.

An aspect of some preferred embodiments of the invention relates to boring a channel through a bone using two opposing needles. One desirable result is that more of the force applied to the needles is utilized to bore into the bone, rather than for pushing the needle away from the bone. In some embodiments, the needles are in a same plane. Preferably, the needles are curved. Alternatively, the needles are straight. In some embodiments, an anvil which does not enter the bone, but which provides a contra-force to the other needle replaces one of the needles.

An aspect of some preferred embodiments of the invention relates to a cross-section of needles used for boring in bone. Preferably the needles are smooth. Alternatively, the needles are grooved. Preferably the cross-section is circular, however, other cross-sections, such as flat-rectangular, triangular and ellipsoid may also be provided. Optionally, the cross-sectional shape varies along the length of the needle, for example providing a spiraling cross-section.

An aspect of some preferred embodiments of the invention relates to inserting a bone-boring needle into a bone at an angle substantially different from a perpendicular. Preferably, two or more needles are provided, facing each other and applying force to the bone at the same time, in opposite directions and having a main force vector pointed towards a common point.

An additional result of entering the bone at the non-perpendicular angle is that, even in a flat or concave bone, the resulting path is not a full half circle, but only an arc of a circle. In some cases, as described herein, a path which is more than a half circle may be bored. Although an arc path is preferred, in some preferred embodiments of the invention other curves may be formed. Further, although the curves are preferably planar, in some embodiments of the invention, the curves are non-planar, for example being bi-planar (each of two halves of the curve in a different plane).

An aspect of some preferred embodiments of the invention relates to a method of boring a hole in a bone in which a cortex of a bone is penetrated using a drill and a medulla of the bone is bored using one or two needles. In a preferred embodiment of the invention, the drills are straight and the needles are curved, so the needles meet inside the bone. Preferably, the drills do not move other that rotation around their axis. Alternatively, the drills travel along a curved path, for example one defined by the needles. Alternatively or additionally to the needles being curved, the needles are straight. In a preferred embodiment of the invention, the needles (and, optionally, the thread) pass through the drill bits.

An aspect of some preferred embodiments of the invention relates to a drill bit for drilling in bone that includes an aperture for the extension of a needle through the aperture in the drill bit. Preferably, the aperture is in the side of the drill bit. In a preferred embodiment of the invention, the drill bit is mounted in a drill head that mechanically synchronizes the angular position of the drill bit and the extension of the needle. Alternatively, when the needles advance, the drill bits arm released to rotate freely, so that the advance of a needle can rotate the drill bit to a desired angular position. Alternatively, an electrical synchronization method is used, for rotating the drill bits a complete number of rotations so that they are properly aligned when they stop. Alternatively, the needle exits through the tip of the drill bit. Optionally, the needle forms a hole in the drill bit when it extends. Alternatively or additionally, the drill bits reciprocate, instead of rotating.

An aspect of some preferred embodiments of the invention relates to a method of transferring power from a power source to a tip of a bone-boring needle. Preferably, the power is applied using a lever. In a preferred embodiment of the invention, a main leverage point is provided at or about the needle. Optionally, a second leverage point is provided further away from the needle and remote from the power source. In a preferred embodiment of the invention, the power source is a human hand that moves a lever relative to a handle. The movement of this handle-lever is transferred, preferably using a cable or a bar to a second lever near the bone-boring needle. One desirable result of providing the leverage near the needle is that a less rugged construction is possible. Possibly, the bone-boring device is flexible rather than rigid.

An aspect of some preferred embodiments of the invention relates to a method of threading a bore. In a preferred embodiment of the invention, two needles are inserted from either side of the bore. The needles meet and when one needle is retracted, it pulls the other needle and a tread attached thereto along with it. In a preferred embodiment of the invention, the needles form the bore when they are inserted. Alternatively, first the bore is formed and then the needles are inserted.

An aspect of some preferred embodiments of the invention relates to a tip exchange mechanism, in which a sharp tip attached to a thread is exchanged between two needles that meet inside a bone. In a preferred embodiment of the Invention, the tip is mounted at the end of a needle and forms a boring tip. When the two needles meet the tip is captured by the other needle and retracts with it, pulling a thread along with it. Alternatively, the tip includes a long flexible extension, to which extension the thread is attached. Optionally, the extension is a super-elastic wire. Thus, the thread is not required to be inside the bone while the needles are in the bone and is less likely to be damaged. Also, such an extension is less likely to tear when the tip is pulled trough the formed bore. Also, in some embodiments contact shearing forces may be applied to the thread. A flexible metallic extension is expected to resist such forces. Thus, a flexible extension may be provided, for example, also for a needle retraction mechanism as above, and not only for tip exchange mechanisms.

An aspect of some preferred embodiments of the invention relates to apertured needle tips for engaging a sharp tip of an opposing needle. In a preferred embodiment of the invention, the apertured tip comprises a bore through the needle, preferably formed when the needle is straight. Alternatively or additionally, the tip is slotted, preferably so that it elastically (or plastically) distorts to engage the opposing tip. In a preferred embodiment of the invention, the bore is not along the axis of the needle, so that bone material that enters the bore at one end, exists at the other end. Preferably the bone material exits within the bone volume, however, in some embodiments it exists inside the device that holds the needle or outside the bone. Alternatively, instead of a through bore, a blind bore is provided. Possibly a hole is provided on the side of the needle, to allow bone matter which enters the aperture to exit through the hole.

An aspect of some preferred embodiments of the invention relates to a retractable tip of a tip-receiving needle. In a preferred embodiment of the invention, a sharp mandrel is placed within the bore of the receiving needle. When the needle is advancing through the bone, the mandrel is preferably advanced, to function as a boring tip for the needle. When the two needles meet, the mandrel is preferably retracted, leaving an aperture at the tip of the receiving needle, to receive the thread carrying tip of the other needle and/or for engaging the other needle.

An aspect of some preferred embodiment of the invention relates to a method of forming a path for a thread in a pair of needles. In a preferred embodiment of the invention, two needles are inserted into a bore and when the needles meet a path is formed, along and/or through the needles from one side of the bore to the other side thereof. A thread is then threaded through or along this path. In a preferred embodiment of the invention, the needles meet end to end. Alternatively or additionally, the needles meet side to side. One needle may be closer to the bone surface than the other at their meeting point or they both might be the same distance from the bone surface but laterally displaced with respect to the surface.

An aspect of some preferred embodiments of the invention relates to providing a bone-boring geometry that is not adversely affected by small errors in the placement of a bone-boring head against a bone. In a preferred embodiment of the invention, this is achieved by providing a needle which rotates on a hinge and providing a resting point of said bone boring head near a center of rotation of the needle. Alternatively or additionally, the invariance is achieved by providing a self-leveling bone-boring head that mechanically aligns itself relative to a bony area against which it is placed. Alternatively or additionally, the invariance is provided by an entire bone boring device being held by a hinged holder, so that the entire device rotates around the hinge to achieve an optimal placement against the bone.

An aspect of some preferred embodiment of the invention relates to a safety mechanism that shelters a sharp tip of a bone boring device, until said tip is to be inserted into a bone. In a preferred embodiment of the invention, the mechanism is controlled from a handle of the device so that the tip is not exposed inadvertently. In a preferred embodiment of the invention, the safety mechanism is a shield that is retracted by applying pressure on the handle of the device. Preferably the applied pressure is also used to activate the device. Alternatively or additionally, the shield is further protected by a safety latch which prevents the pressure from being transferred to the shield unless the latch is in an "armed" state. Alternatively or additionally to a retracting shield, it is the sharp tip which is selectively retracted and advanced, relative to a shield, so that it does not engage tissue unless a desired sequence has been performed.

In a preferred embodiment of the invention, the device is designed to support the following sequence: first the needles are urged towards the bone, so that they compress any soft tissue between them and the bone and then the needles are advanced through the soft tissue (if necessary) to bore a hole through the bone.

An aspect of some preferred embodiments of the invention relates to a safety feature for preventing damage to or from circular needles that are inserted in a bone. In a preferred embodiment of the invention, when a device coupled to said needles is released, the releasing action first retracts the needles and only then allows the device to be moved.

An aspect of some preferred embodiment of the invention relates to sensing and remotely indicating when certain spatial configurations of a bone borer are achieved. In a preferred embodiment of the invention, when these configurations sensed, a visual and/or audible indication is displayed to a surgeon. Alternatively or additionally, when these configurations are sensed, a function of the borer is locked and/or unlocked. One example of a sensed spatial configuration is an angle of the borer head relative to the bone. Another example is determining if two boring needles meet in the bone in a desired manner.

There is thus provided in accordance with a preferred embodiment of the invention a bone boring device, comprising:
  a hinge;
  a handle coupled to said hinge;
  at least one curved needle having a tip at one end thereof and rotatably mounted on the hinge, wherein when said tip is placed against bone and said needle is rotated on said hinge, said needle is urged into said bone. Preferably, the device comprises a resting point adjacent said hinge, which resting point is adapted to be placed against said bone. Alternatively or additionally, said curved needle has a radius of curvature matching a distance of said needle from said hinge.

In a preferred embodiment of the invention, said at least one needle comprises a first needle and a second needle. Alternatively or additionally, said needles rotate about a same hinge for urging into said bone. Alternatively, said needles do not share a-hinge.

In a preferred embodiment of the invention, said needles are adapted to meet at their ends, when said needles arm rotated around said hinge. Preferably, said needles are formed with a conduit therein and wherein, when said needles meet a continuous conduit is formed along the needles. Preferably, the device comprises a channel substantially contiguous with said bore and adapted for advancing a thread through said channel and along said conduit.

In a preferred embodiment of the invention, said needles meet tip-to-tip. Alternatively, said needles meet side-to-side at their ends.

In a preferred embodiment of the invention, the device comprises a thread pusher for advancing thread through said bore. Preferably, said thread pusher extends to outside said device.

In a preferred embodiment of the invention, said first needle is adapted to engage a tip of said second needle. Preferably, said second needle is hollow. Alternatively or additionally, said second needle has a grove defined along most of its length.

In a preferred embodiment of the invention, said tip comprises a detachable tip to which the thread is attached. Preferably, said detachable tip comprises an extension to which a thread is attached, which extension is substantially longer than said second needle.

In a preferred embodiment of the invention, said second needle is detachable from said device. Preferably, said needles meeting causes said second needle to detach. Preferably, said second needle is adapted for attaching a thread thereto.

In a preferred embodiment of the invention, said first needle defines an aperture at its tip, which aperture is adapted to engage said tip. Preferably, said aperture is an opening to a blind hole. Alternatively, said aperture is an opening to a through hole.

In a preferred embodiment of the invention, said aperture connects to a hollow volume along an axis of said needle. Preferably, the device comprises a sharp-tip mandrel that fills said hollow volume. Preferably, said mandrel is retracted when said needles meet.

In a preferred embodiment of the invention, said aperture connects to a hollow volume oblique to an axis of said needle.

In a preferred embodiment of the invention, said aperture is an opening to a volume extending into said needle and having a substantially constant inner diameter.

In a preferred embodiment of the invention, said aperture is an opening to a volume extending into said needle and having an inner diameter that increases away from the aperture.

In a preferred embodiment of the invention, said aperture is an opening to a slotted volume.

In a preferred embodiment of the invention, said needles and said-hinge are comprised in a disposable cartridge, separable from said handle.

There is also provided in accordance with a preferred embodiment of the invention, a method of boring a path in a bone, comprising:

providing at least one curved needle having a tip and an axis;

positioning said needle at a position adjacent the surface of said bone, such that said axis at the tip is not perpendicular to said surface; and advancing said needle to bore a hole into said born. Preferably, boring a hole comprises boring a hole without removing bone tissue. Alternatively or additionally, said at least one needle comprises two needles. Alternatively, said at least one needle comprises only one needle.

There is also provided in accordance with a preferred embodiment of the invention, a bone boring device, comprising:

at least one needle adapted for boring into bone;

a force providing element remote from said needle, for advancing said needle,; and a force amplifier, coupled to said needle and adjacent to said needle which amplifies force provided from said force providing element and supplies it to said needle. Preferably, said at least one needle comprises two needles. Alternatively or additionally, said needle is mounted on a hinge and wherein said needle is rotated around said hinge by force provided by said force amplifier. Preferably, said force amplifier comprises a lever.

There is also provided in accordance with a preferred embodiment of the invention, a method of attaching a suture to a bone, comprising:

advancing two needles into said bone to meet inside said bone;

advancing a thread along a common bore defined by said needles after said needles meet; and retracting said needles.

There is also provided in accordance with a preferred embodiment of the invention, a method of attaching a suture to a bone, comprising:

advancing two needles into said bone to meet inside said bone;

engaging, by one of said needles the other of said noodles, which other needle has a thread attached to a portion thereof; and retracting said one needle, such that at least said portion is carried along by said one needle with said attached thread. Preferably, said portion comprises a tip of said needle.

In a preferred embodiment of the invention, said portion comprises a detachable tip of said needle, which tip includes a thin extension substantially longer than-said needle, wherein said tread is attached to a portion of said extension distal form said detachable tip. Alternatively or additionally, said portion comprises an entire extent of said needle which enters said bone.

There is also provided in accordance with a preferred embodiment of the invention, a bone-boring device, comprising:

at least one curved needle adapted for extending to bore a hole in a bone;

a base holding said needle and adapted for being placed against a bone;

a handle coupled to the base; and a needle retractor, which retracts said needle when a force on said handle in a particular direction is lower than a predetermined amount, prior to said base retreating from said bone i response to a lowering of the force.

There is also provided in accordance with a preferred embodiment of the invention, a bone-boring device, comprising:

at least one curved needle adapted for extending to bore a hole in a bone;

a base holding said needle and adapted for being placed against a bone a handle coupled to the base; and a needle advancer, which advances said needle only when a force on said handle in a particular direction is higher than a predetermined amount, said predetermined force assuring that said base is urged against said bone.

There is also provided in accordance with a preferred embodiment of the invention, a detachable tip for a needle, comprising:

a tip having a sharp end and adapted for insertion through a bone; and a flexible extension of said tip, opposite of said sharp end and substantially longer than said sharp tip, attached to a thread. Preferably, said tip is adapted for being grasped by a hollow needle, at a side thereof of the extension. Alternatively or additionally, said sharp end is adapted for being grasped by a hollow needle, at a side opposite of the extension.

There is also provided in accordance with a preferred embodiment of the invention, a self-aligning device for boring into bone, comprising:

a boring head having at least two boring tips;

a body;

a handle attached to said body;

a hinge coupling said head to said body at a location substantially equidistant from said boring tips. Preferably, said boring tips comprise drill bits. Alternatively or additionally, said boring tips comprise boring needles.

In a preferred embodiment of the invention, said head includes a power source for activating said boring tips. Alternatively or additionally, said boring tips face said handle.

There is also provided in accordance with a preferred embodiment of the invention, a method for forming a channel in a bone, comprising:

drilling two holes in a cortex of the bone; and advancing at least one needle through said drilled holes through a medulla of said bone. Preferably, said holes are perpendicular to a surface of said bone. Alternatively or additionally, said at least one needle comprises two needles that meet inside the bone.

There is also provided in accordance with a preferred embodiment of the invention, apparatus for forming a channel in a bone, comprising:

at least one drill bit for drilling into a bone and defining a channel formed therethrough and an aperture from the outside of said bit to said channel; and at least one needle adapted to fit through said aperture. Preferably, said at least one drill bit comprises two drill bits. Preferably, said drill bits are parallel.

In a preferred embodiment of the invention, said at least one needle comprises at least two needles. Alternatively or additionally, said at least one needle comprises a curved needle.

In a preferred embodiment of the invention, said aperture is on a side of said drill bit.

BRIEF DESCRIPTION OF THE DRAWINGS

The invention will be more clearly understood by reference to the following description of preferred embodiments thereof in conjunction with the figures, wherein identical structures, elements or parts which appear in more than one figure are labeled with the same numeral in all the figures in which they appear, in which:

FIG. 5A illustrates an end to end needle configuration, in accordance with a preferred embodiment of the invention;

FIG. 5B illustrates various needle cross-sections for the configuration of FIG. 5A;

FIGS. 6A and 6B are a side and a top view, respectively of a side-by-side needle configuration, in accordance with a preferred embodiment of the invention;

FIG. 7A illustrates a top-bottom needle configuration, in accordance with a preferred embodiment of the invention;

FIG. 7B is a cross-sectional view along line B—B In FIG. 7A, showing a detail of the needle configuration;

FIGS. 16A and 16B illustrate a combined drilling and needle boring head in accordance with a preferred embodiment of the invention;

DETAILED DESCRIPTION OF PREFERRED EMBODIMENTS

Figure 1B:
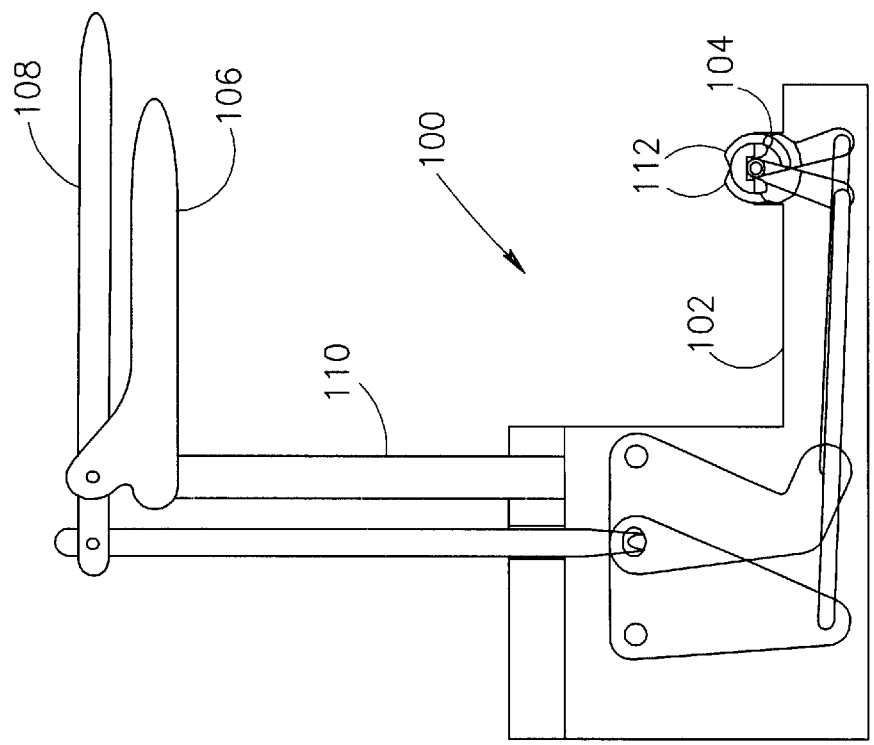
FIGS. 1A and 1B are schematic illustrations of a bone-boring device, in un-activated and an activated configuration, respectively, in accordance with a preferred embodiment of the invention.
Figure 1A:
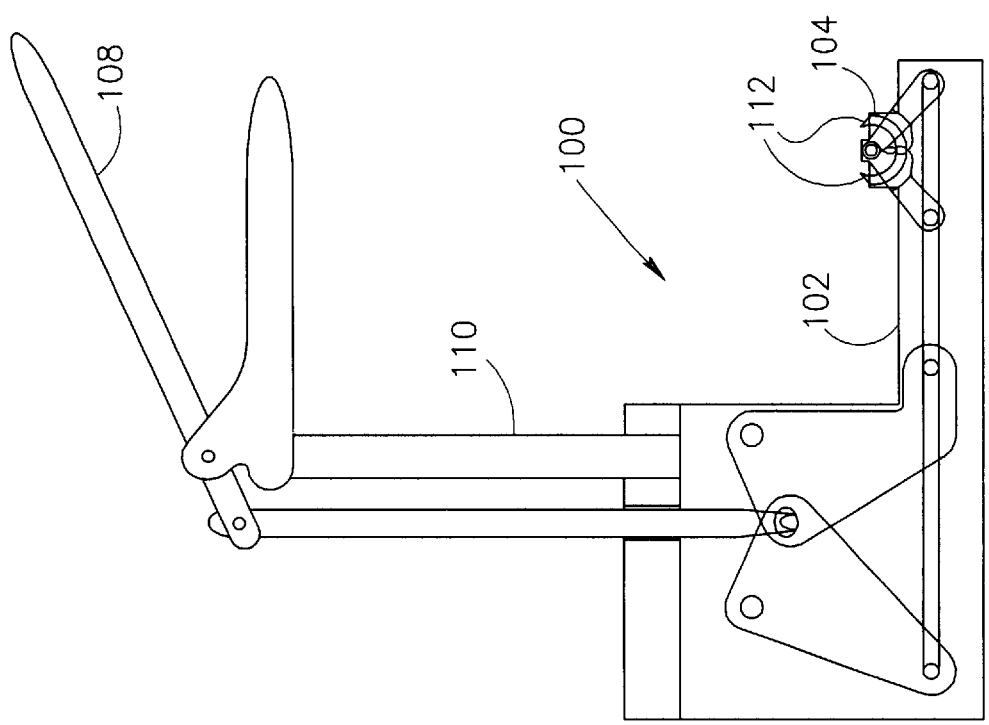

FIGS. 1A and 1B are schematic illustrations of a bone-boring device 100, in unactivated and activated configurations, respectively, in accordance with a preferred embodiment of the invention. Device 100 generally comprises a base 102 including a bone-boring head 104, a handle 106, possibly including a lever 108 and a shaft 110 interconnecting the handle and the base. In FIG. 1A, a pair of needles 112 of bone-boring head 104 are retracted. In FIG. 1B, when lever 108 is moved towards handle 106, needles 112 rotate and extend, boring a hole in adjacent bone.

The device shown in FIGS. 1A and 1B is suitable for attaching sutures to an inside face of a pubic bone. Thus, needles 112 extend towards the handle. In use, boring-head 104 is placed against the pubic bone, upwards pressure being applied to handle 106 to assure good contact between the boring head and the bone, and then lever 108 is depressed to advance needles 112 and bore the hole. In devices for other uses, bone-boring head 104 may extend away from handle 106 or at a different orientation hereto and may even be adjustable between several orientations.

Figure 2:
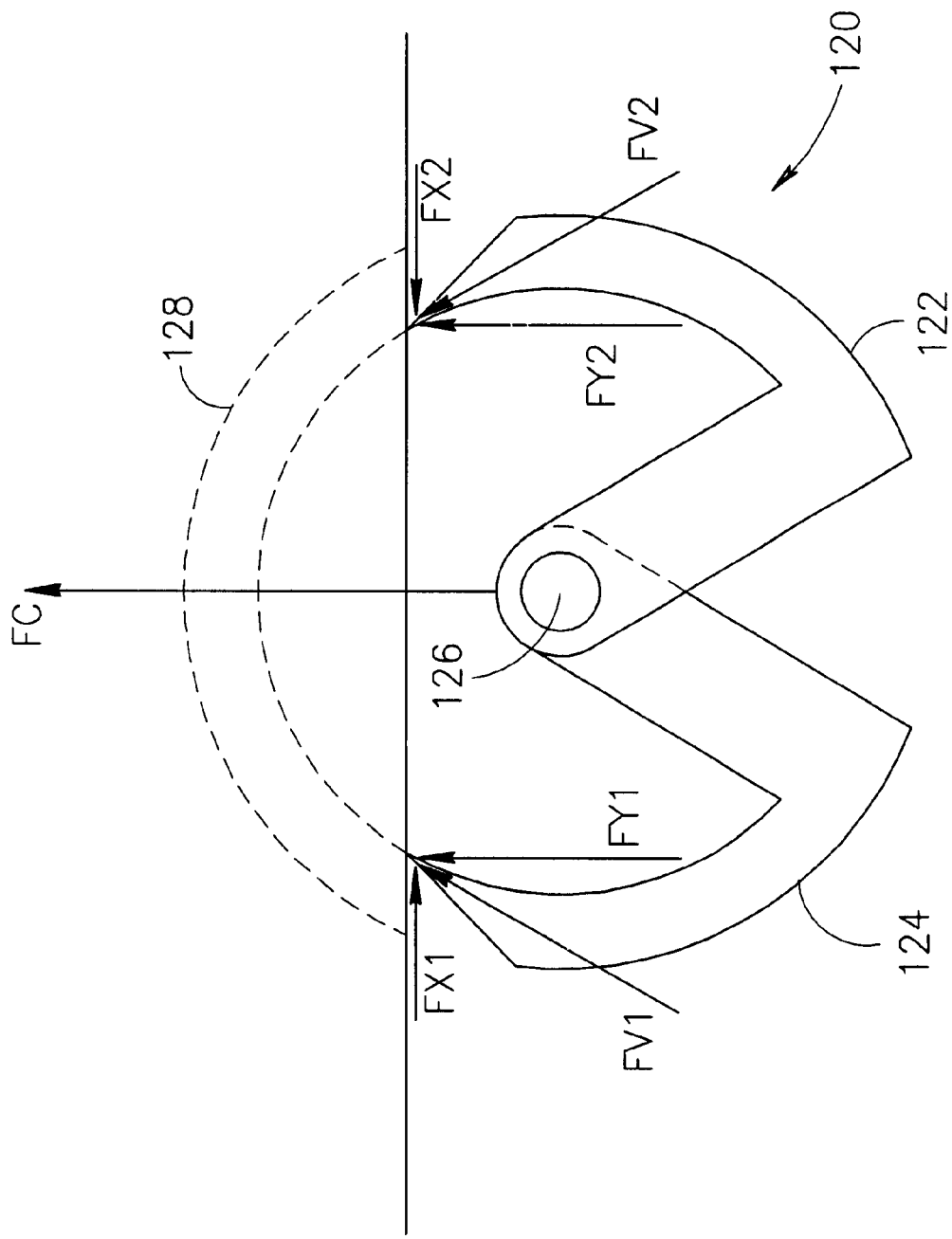
FIG. 2 is a schematic illustration of a hinged dual-needle boring-head, in accordance with a preferred embodiment of the invention.

FIG. 2 is a schematic illustration of a hinged dual-needle boring-head 120, in accordance with a preferred embodiment of the invention. Preferably, head 120 comprises a needle 122 and a needle 124 that share a common hinge 126. When the needles rotate around the hinge, they form a channel 128 in the bone.

In a preferred embodiment of the invention, the needles are arranged to enter the bone at a non-perpendicular angle thereto. Thus, forces applied by the two needles to the bone cooperate for drilling a bore. In the figures rotation of needle 124 around its hinge applies a force vector FV1, which can be represented by its components FX1 and FY1. Similarly, needle 122 applies a force vector FV2, represented by components FX2 and FY2. An additional force FC is applied by the needles (or by a resting point 134, FIG. 3A below) as a result of a physician urging boring-head 120 against the bone. Force FC is also found in a needle that is directed perpendicular to the bone. FC urges the needle into the bone. However, as the bone has a large resistance to penetration by the needle, a large FC is required to effect that entry, which force is applied from outside the body. In addition, the force applicator is not stable, allowing the needle to slip and/or penetrate at an undesirable angle and/or form an undesirable channel.

In the embodiment shown, forces FX1 and FX2 are in opposing directions, thus stabilizing head 120 from moving. Also, it is noted that the channel is not perpendicular to the bone surface but also includes a significant X component, already at its start. Thus, once the needles enter the bone, or if the bone is not smooth, the FX forces can start boring in the desired direction immediately. Further, if the FX forces engage the surface, the FY forces can start boring, even without an FC force (or with a reduced one) to hold the needles against the bone, since the bone, overlying the needles, holds them in place. Further, if the needles arm forced through soft tissue, once the soft tissue is pierced, the soft tissue assists in holding the needles against the bone.

Additionally, forces FY1 and FY2 are generated at the boring-head and are typically, but not necessarily, smaller than force FC. The application of forces FY1 and FY2 is at least somewhat decoupled from the FC force, making them easier to control, so that increasing these forces or decreasing them (for example by a sudden give of the bone) do not necessarily affect the application of force FC to the handle. Thus, the bone boring head is more stable.

Figure 3B:
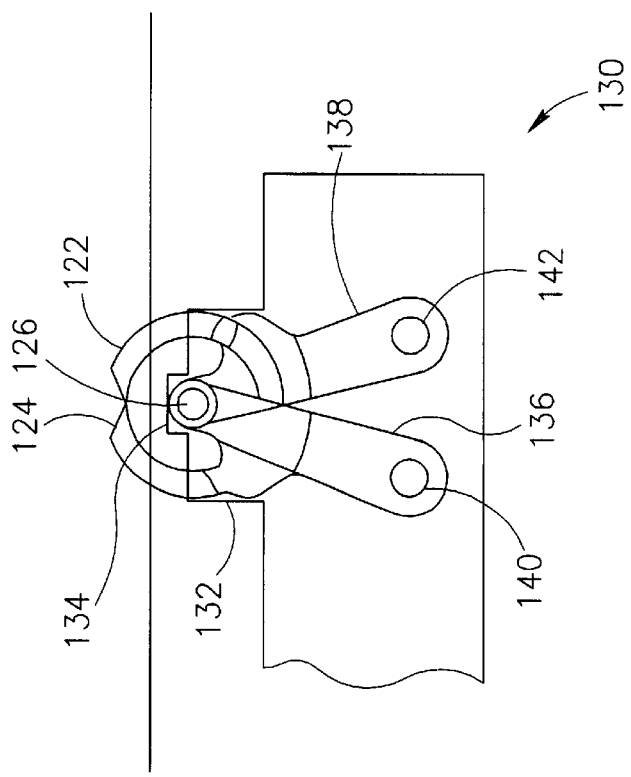
FIGS. 3A and 3B illustrate the action of a leveraged hinged dual needle boring head, in accordance with a preferred embodiment of the invention.
Figure 3A:
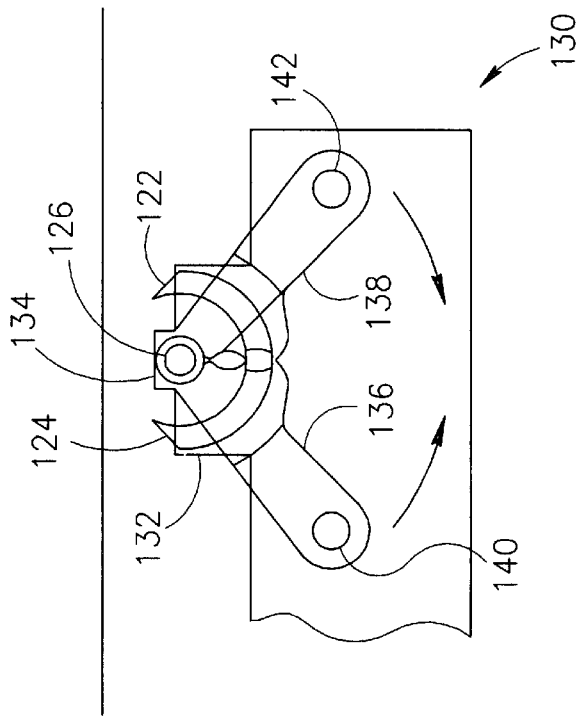

FIGS. 3A and 3B illustrate the action of a leveraged hinged dual needle boring head 130, in accordance with a preferred embodiment of the invention, in this embodiment, not only are the bone-penetration forces generated near the head, but also any force amplification necessary for generating these forces is also performed near the head, 80 that there is less variation in the force that is transferred along the device. Thus, a more stable and/or easy to use device is provided.

In head 130, force amplification and/or transduction is provided by translating substantially linear motion of a lever 136 and it lever 138 into rotation of needles 122 and 124. In a preferred embodiment of the invention, lever 136 and needle 122 are-formed of a single piece of material, possibly increasing reliability and/or reducing cost. In a preferred embodiment of the invention, the linear force is applied to levers 136 and 138 using anchors 140 and 142, for example holes. A shield 132 preferably prevents the needle tips from engaging tissue when the needles are retracted. Alternatively (and as shown), the tips of the needles may peek out beyond the shield, but possibly not beyond the resting point 134 (described below).

As can be appreciated from FIGS. 2 and 3A–3B, different needle tip force geometries will have different mechanical properties with respect to entering a bone. Different medical situations, bone types, bone surfaces and/or other considerations may require different bore-head configurations. Parameters that can varied may include one or more of the following:

(a) the attack angle of the needles, and especially of the tip thereof, which can affect the force vectors at the tip (i) when the needle enters the bone and (ii) when the needle travels through the bone, the effect of the attack angle being, for example, neutral, urging the needle towards the hinge, urging the needle away from the hinge or urging the needle in a plane perpendicular to the needle;

(b) penetration depth, i.e., a distance between where the needles meet inside the bone and a resting point 134 of the bore-head against the bone surface (shown slightly separated from the surface, for clarity of presentation);

(c) distance between the entry holes;

(d) leverage (affected by the lengths of both the levers and the needles);

(e) cross-section of the needle tip and the needle as a whole (will be described in greater detail below);

(f) threading behavior of the needles (described in greater detail below);

(g) radius of rotation; and (h) a degree of symmetry between the parameters of the two needles, for example causing one needle to bore easier than the other.

Figure 3C:
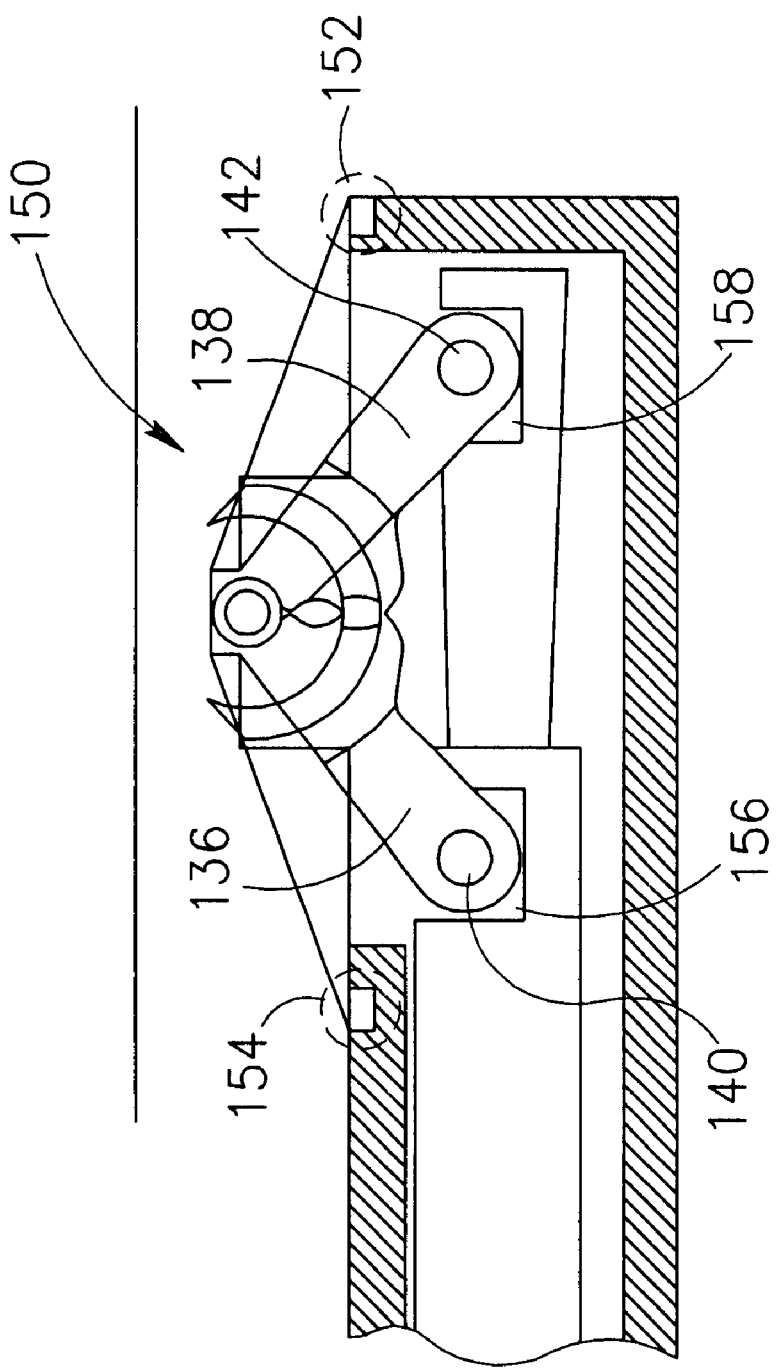
FIG. 3C illustrates a replaceable needle-boring head, with needles retracted and with needles extended, in accordance with a preferred embodiment of the invention.

In a preferred embodiment of the invention, a plurality of replaceable boring-heads is provided, each head having different parameter values. FIG. 3C illustrates a replaceable needle-boring head 150, in accordance with a preferred embodiment of the invention. A plurality of matching protrusions and depressions 154 and 152 are preferably provided on the boring head and on the base of the device, to align the head and the device. In a preferred embodiment of the invention, a coupler 156 and a coupler 158 are provided at the ends of force transmission bars (described in FIGS. 4A and 4B) which engage anchors 140 and 142. Preferably the coupler is a snap coupler which can be separated by the application of sufficient force.

Alternatively, the boring head includes means for adjusting one or more of the above parameters. In one example, the penetration depth can be adjusted by increasing a distance between resting point 134 and hinge 126, for example using a screw mechanism. This also affects the distance between the entry holes of the needles.

It should be noted that the two needles may have different cross-sections, different radii of rotation, different leverage, different angles of attack (penetration of the tip) and/or other characteristics in which they different. In some preferred embodiments of the invention, however, the needles are substantially the same. In addition, although the two needles can use different hinges, possibly with a controllable distance (in the X and/or Y axes) between the hinges, in a preferred embodiment of the invention, a single hinge is shared by the two needles, as shown.

Figure 4B:
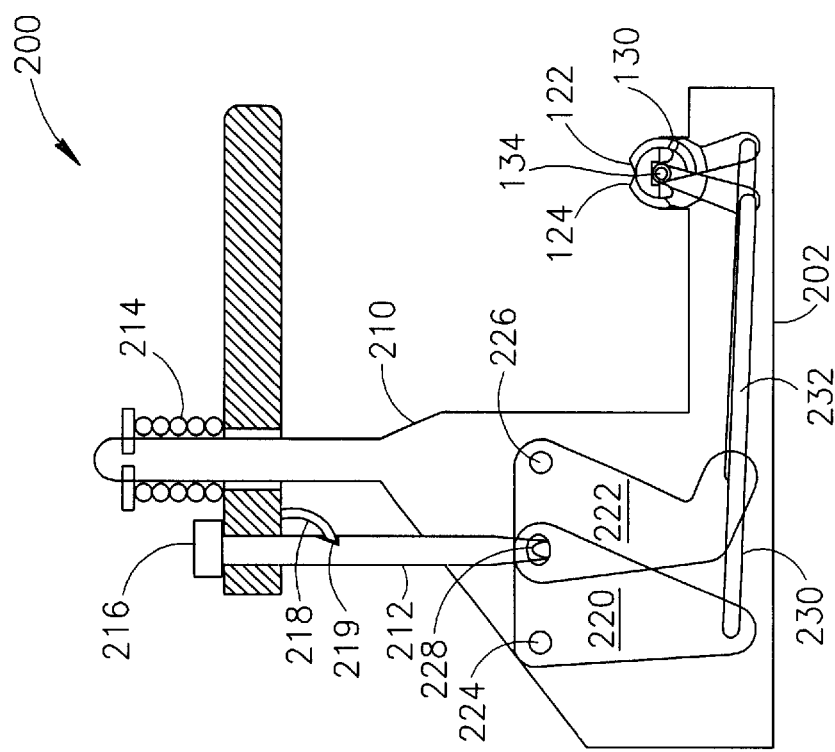
FIGS. 4A and 4B schematically illustrate a bone-boring device having a needle extension/retraction mechanism which matches a particular activation logic, in accordance with a preferred embodiment of the invention.
Figure 4A:
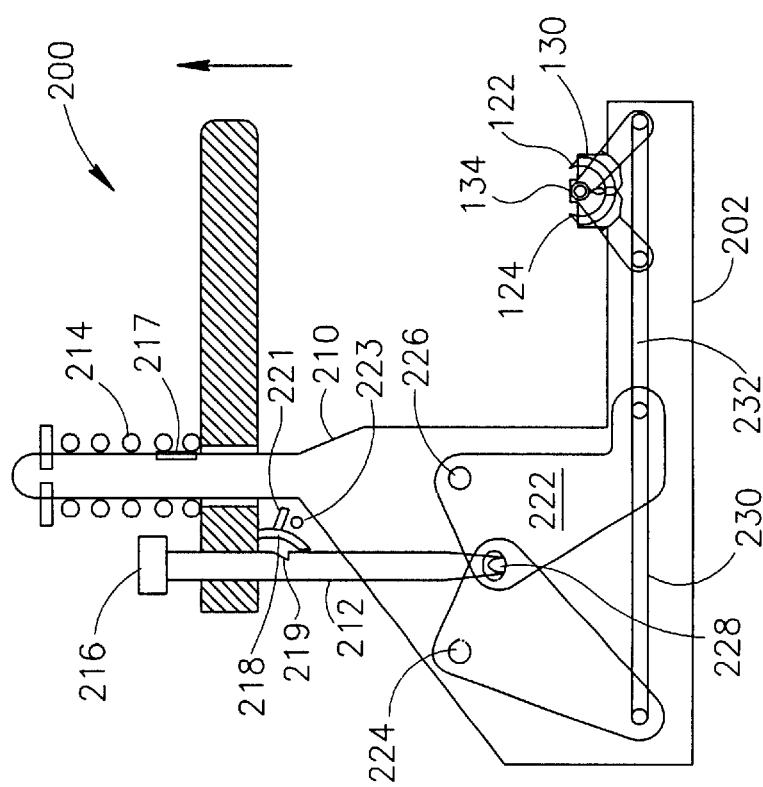

FIGS. 4A and 4B schematically illustrate a bone boring device 200, in accordance with an alternative preferred embodiment of the invention. Device 200 comprises a base 202 having a boring-head such as boring head 130, mounted thereon. Base 202 is connected to a shank 210, having a lever 206 coupled thereto. A contra-force spring 214 couples lever 206 to shank 210. In use, head 130 (actually resting point 134) is placed against a pubic bone (not shown). Lever 206 is pulled away from the boring head against the resistance of spring 214. At this stage, the motion of lever 206 only urges resting point 134 against the pubic bone (the force being transmitted by spring 214), compressing intermediate tissue. Preferably the motion of lever 206 does not extend the needles. After a short travel distance, handle 206 engages an engager, such as a protrusion 216 provided on a force-transferring element 212. Once engaged, further motion of lever 206 causes force to be transmitted to element 212 and hence to boring head 130, causing the needles to extend. In a preferred embodiment of the invention, a peg (or other type of latch) 218 further couples lever 206 to force transferring element 212 via an indentation 219 in element 212.

Element 212 rotates one, possibly two levers 220 and 222 around their respective hinges 224 and 226, thereby causing a bar 230 and a bar 232, coupled to the levers, to move along the base and transfer force to the levers of the boring-head (which move as described above with reference to FIGS. 3A and 3B). As shown, the configuration of the two levers reduces the transferred force. However, in other preferred embodiment of the invention, the levers increase the transmitted force, while reducing the travel distance.

When lever 206 is released, peg 218 forces the needles to be retracted, before reducing the pressure of head 130 against the pubic bone. Thus, there is less likelihood of the needles damaging the bone after the bone boring is completed. In a preferred embodiment of the invention, once the needles are retracted, peg 218 is disengaged (for example by an inclined portion 221 of the peg when it is urged against a protrusion 223) and device 200 can be removed from the pubic bone. Alternatively, peg 218 does not disengage, so that device 200 is substantially a one-use device. Alternatively, peg 218 is disengaged by a specially provided control, such as a button, to prevent inadvertent reuse of the device before the physician is ready for another bone-boring process.

Alternatively or additionally to the specially provided control, a safety latch may be provided which does not allow lever 206 to travel far enough along shank 210 to extend the needles, unless the latch is released. Thus, inadvertent damage to tissue by the needles is less likely. Alternatively or additionally to the safety latch, a pin (not shown) may be provided at or about resting point 134, which pin, if depressed with sufficient force, causes the needles or their levers to engage the bars 230 and 232. If an insufficient force is presented, the needles are not coupled to the bars and cannot be extended. Possibly, a spring is provided at the needles, which spring retracts the needles from the bone if no opposite force is provided by the bars. Thus, if there is insufficient pressure on the pin, the needles are retracted. Such a pin may act in a purely mechanical fashion or may include an electrical circuit to alert the operator and/or actively retract the needles.

It should be noted that a designated resting point 134 is not required. However, in many cases it is desirable that the needles be completely retracted and some element is generally required for compressing intermediate soft tissue and/or for stabilizing the boring head.

In devices not meant for the pubic area, or in devices in which boring head 130 can point away from lever 206, spring 214, protrusion 216 and peg 218 may need to be replaced and/or augmented by suitably located elements which perform their functions, in a reverse direction. Additionally, various deigns of handles, for example axial or perpendicular to the device body may be provided.

Element 212 is shown as a bar. However, it is noted that most of the force is applied when extending the needles. Thus, element 212 may have its function served by a wire, preferably with a retraction spring for retracting the needles when lever 206 is released.

Alternatively or additionally, bars 230 and 232 may be replaced by wires. Possibly, a coaxial wire pair is used, in which the inner wire is attached to one lever and the outer one to the other lever. Thus, boring head 130 can be more easily twisted around base 202 and/or otherwise moved. Optionally, a spring is provided to retract the needles once they are extended.

As can be appreciated, the resistance of spring 214 is related to the total force applied against the pubic bone. In a preferred embodiment of the invention, the tension in spring 214 can be adjusted to require a physician to apply a desirable minimum pressure against the pubic bone. Alternatively or additionally, the linearity of the spring and/or the force constant of the spring may be varied to match a desired profile of applying force to the needles and/or to provide better controllability of the force. In one example, a large force is required to enter the bone, but, once the bone is entered, possibly less additional force is required to continue the boring. In general, it is possible to control the amount of compression force applied to the soft tissue before and after the needles advance, by suitable varying the parameter of the spring, motion of the lever 206 and the force amplification of the power train to the needles.

In some cases it is desirable that the physician be provided with a tactile indication of the extension of the needles. This may be achieved by putting a protrusion on shank 210, under spring 214 at a point corresponding to the extension of the needles. Thus, as the lever is pulled a "bump" is felt at that point. Additional such protrusions may be provided at other points on the shank, for example at a point where the needles are fully extended and no further force is required. Alternatively or additionally, to these burns transmitting feed-back to the physician, the bumps may be used to control the device, for example as a safety mechanism that allows the needles to extend or as a control which "fires", the thread (as described below). Alternatively or additionally, a large protrusion 217 is provided underlying spring 214 and frictionally engaging lever 206, so that compressing the soft tissue will be more difficult than advancing the needles. Possibly, the protrusion applies more friction when the lever is pulled than when the lever is released, for example by suitable machining of its surface. In an exemplary device the various parameters, such as spring constant, amount of motion and needle leverage are adapted so that a 100N force is required to compress the soft tissue prior to the extension of the needles. An additional force of 40N is preferably required for extension of the needle trough a typical pubic bone. The total motion of the lever is 10 mm for compressing the tissue and 4 mm for extending the needles.

Although this embodiment is shown with a single lever 206, a non-movable handle may also be provided, for example for co-gripping with lever 206. Also, instead of manual forces used to power the needle head, air-pressure, electric or other types of power sources may be used.

Once the needles meet, a channel is created in the bone and a thread can be passed through the channel. In a preferred embodiment of the invention, the thread is passed through a channel forming in and/or along the body of the needles. The thread may be inserted with the needles, while they bore, or after the boring is completed. Alternatively, the device is used only to bore a hole in the channel and not to pass a thread, which may be passed manually, for example, if so desired, preferably after the needles are removed.

FIG. 5A illustrates an end to end needle configuration, in accordance with a preferred embodiment of the invention. A needle 240 and a needle 242 meet end to end. It should be appreciated that in accordance with some preferred embodiments of the invention, better control over the final location of the needles is possible if the needles are rigidly attached to a single hinge than if they do not use hinges or are attached to separate hinges.

Needles 240 and 242 preferably comprise an inner bore, such that when they meet end to end, a path 241 is formed there through.

FIG. 5B illustrates various suitable cross-sections for needles 240 and 242. Cross-sections 248 and 246 are triangular cross-sections, having a circular inner bore. Cross-section 250 is circular, with a circular inner bore. Cross-section 252 is an example of an open-bore needle, having a "U" shaped cross-section, with the bore on the inside of the "U". In some embodiments, a groove on the side of a substantially solid needle is used instead of a deeply grooved cross-section such as a "U". It is noted that the cross-section of the needle may vary along the needle, for example, there being a groove for the thread along most of the needle and an inner bore only at the needle tip. Alternatively or additionally, the tip of one needle may be narrow enough to enter the tip of the other needle, forming an inside-outside matching. In an alternative embodiment described below, one needle has a removable tip, to which the thread is attached, which tip is captured by the other needle. The attachment method can be, for example, using a knot, in a crevice in the tip or using other methods of attaching a thread to a metal object, as known, for example, in the art of bone anchors.

Optionally, the base of the needles is cleaned out, for example using suction, forward flow of a saline solution or an advancing mandrel, to remove bone debris that accumulates in the bore. An opening at the side of the needle may be provided for the exit of such material, or such a hole may be defined when the two needles meet. Alternatively, a somewhat rigid thread pusher is provided, which can push the bone debris ahead of it self or form a channel in the debris.

FIGS. 6A and 6B are a side and a top view of a side-by-side needle configuration, in accordance with a preferred embodiment of the invention. In the embodiment shown in FIG. 6A, a needle 254 and a needle 252 overlap at an area 256 thereof. A bore-258 is formed from the bores of the individual needles. In a preferred embodiment of the invention, the bore of the individual needles do not reach the tip of the needle but exit the needle at its side near the tip, so the tip can be solid. When the two needles overlap properly, the bore exits meet and bore 258 is formed.

In some embodiments, when the two needles ac retracted, the retracting solid tips may shear the thread between them. One possible solution is that the tip has a smaller cross-section then the rest of the needle Another possible solution is providing a metallic read pusher or thread, which is less likely to be sheared. Alternatively or additionally, the inside faces of the tips are inclined, so the shear forces on the thread are gradual and smaller. Alternatively or additionally, the two needles have different radiuses or rotation and/or the hinge is not at their center of curvature, so that when they retract, they move apart. Such moving apart can also be achieved by using needle tips that are not symmetrical, so that when they are advanced and/or retracted through bone, a force is generated perpendicular to the line of motion of the needle.

FIG. 7A illustrates a top-bottom needle configuration, in accordance with a preferred embodiment of the invention. Instead of or in addition to the needles being side-by-side in a plane perpendicular to the needle plane, the needles are one on top of the other (or inside the other, with respect to the view from the hinge), effectively being side-to-side in the plane of the needles. In the embodiment shown, a needle 264 is inside a radius of needle 262, and the two needles overlap at an overlap area 266. FIG. 7B illustrates various possible bores for the overlap area, for example two opposing "U"-shaped bores (268) or two opposing "V" shaped bores (270). This bore may be open for the entire length of the needle or only at the overlap area.

In a preferred embodiment of the invention, the radius of needle 264 is smaller than the radius of needle 262, when measured from the hinge. Alternatively or additionally, the needles are not perfect arcs and/or the radius of the needles does not match the radius of rotation. Properly configured, such construction will cause the needles to engage each other when they meet at overlap 266, instead of sliding over each other. A similar result can be achieved with side-by-side needles, where the needles do not travel in exactly parallel planes, so once they meet, further movement is difficult or impossible.

Figure 8A:
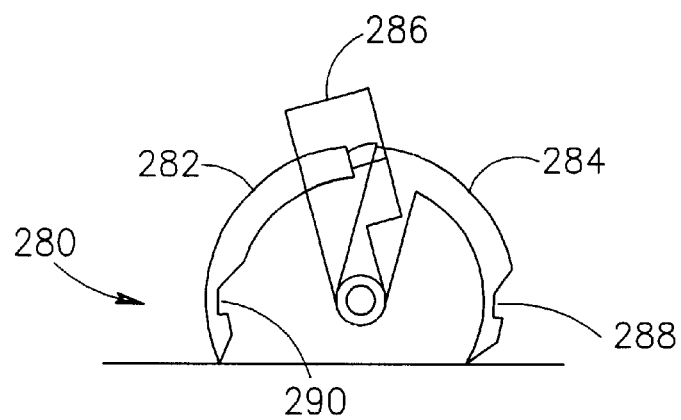
FIGS. 8A–8C illustrate a detachable needle configuration, and its use in boring and threading a bone, in accordance with a preferred embodiment of the invention.
Figure 8B:
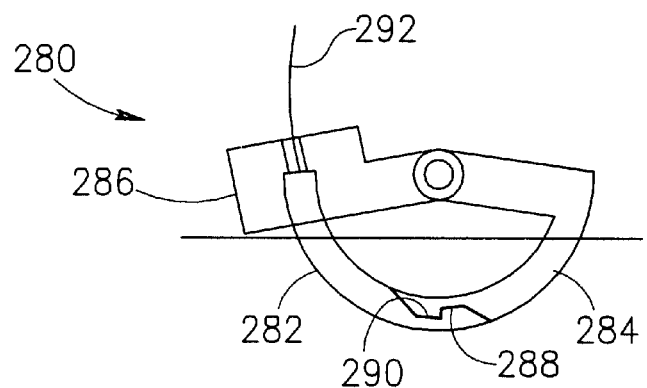
Figure 8C:
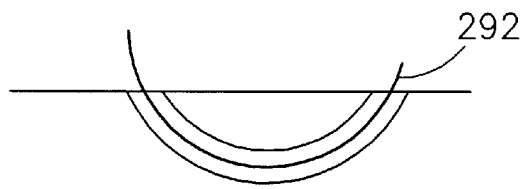

FIGS. 8A–8C illustrate a detachable needle configuration 280, and its use in boring and threading a bone, in accordance with a preferred embodiment of the invention. Configuration 280 includes a non-detachable needle 284, and a detachable needle 282, mounted on a base 286. Needle 284 includes a tip 288 and needle 282 includes a tip 290; these tips are designed to engage, once they meet. Although a particular engagement design is shown, others may be used, for example tip 288 enters into a bore in tip 290 and one or both tips are elastically or plastically deformed so that the tips engage.

As shown in FIG. 8B, once the needles are inserted into the bone, they bore a path and then meet, locking. When the needles are retracted, needle 282 stays latched to needle 284 and is pulled out along the path of needle 284, rather than back along its path. Preferably, a thread 292 is attached to needle 282, such that the thread is pulled along by needle 282 when it advances. Many methods are known in the art for attaching a thread to a needle.

FIG. 8C shows the result of the process, which is a path threaded by a thread 292.

It should be noted that not all of needle 282 needs to be detachable. Rather, it is enough that any part to which the thread is attached is detachable. Thus, in some embodiment, only the tip of needle 282 is detached. Preferably, a groove or a bore is defined in needle 282, so that the boring in the bone does not damage the thread. Also, although needle 284 is portrayed as non-detachable, in some embodiments, it may be desirable to allow needle 284 to be detachable, for example outside the body, for replacement thereof.

In a preferred embodiment of the invention, needle 282 includes a safety latch that releases the needle only if the needle is actually engaged by needle 284, so that needle 282 is not inadvertently left in the bone.

Figure 8D:
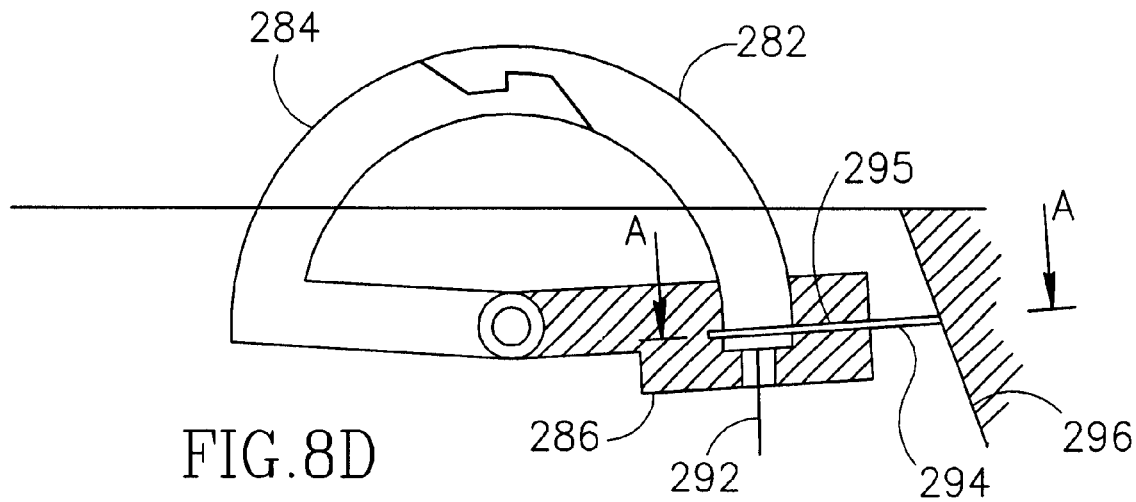
FIGS. 8D–8F illustrate a safety latch which releases the detachable needle of FIGS. 8A–8C only if the two needles meet, in accordance with a preferred embodiment of the invention.
Figure 8E:
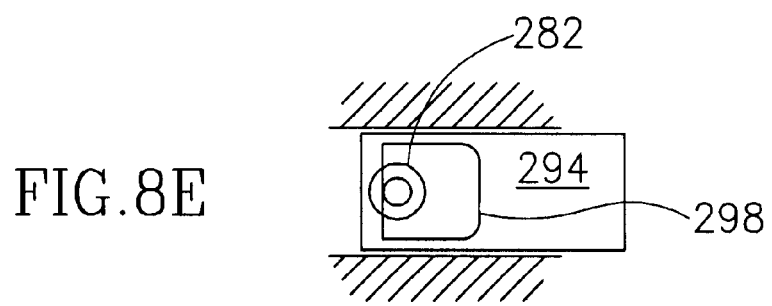
Figure 8F:
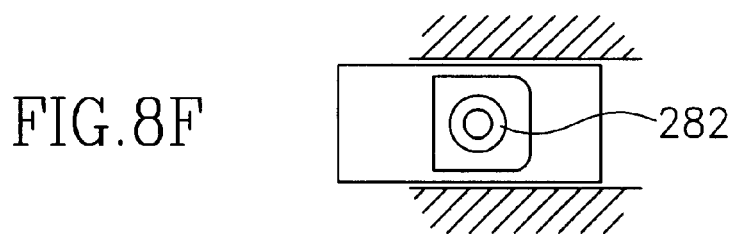

FIGS. 8D–8F illustrate a safety latch which releases the detachable needle of FIGS. 8A–8C only if the two needles 282 and 284 meet, in accordance with a preferred embodiment of the invention. In the exemplary latch shown, a pin 294 is arranged in a slot 295 in base 286. The base of pin 294 is possibly urged against an incline 296, for example using a spring (not shown). Alternatively to an incline, a flexible pin may be provided which is attached to a fixed location. As needle 282 is advanced, pin 294, urged by the incline, slides in slot 295. At a certain point, the motion of pin 294 releases needle 282. FIG. 8E shown a method in which pin 294 has an aperture 298 formed therein. When the pin is moved, shown in FIG. 8F, the needle is disengaged from the pin and can be extracted by needle 254 that engages it.

Alternatively or additionally, to a mechanical latch, an electrical sensor may be used. This sensor senses when the noodles meet, for example from the amount of motion of the needles. Alternatively, the sensor directly senses the contact between the needles, for example by measuring a reduced electrical resistance when the needles meet. The signal generated by this sensor can have one or more uses, including indicating to a physician that contact was made (preferably using a light or a sound), freeing the detachable needle or "firing" a thread (described below).

In a preferred embodiment of the invention, the needles described above are pushed into the bone and they form a channel by forcing through the bone, rather than by removing bone material. Alternatively, in some cases, the needle cross-section may be selected so that the needle removes and/or pulverizes bone when the needle advances. Preferably, the needle's cross-section, especially at the tip, matches the direction of fibers in the bone, so that it can better enter the bone without cutting across fibers. Preferably, one or both needles are smooth. Alternatively, a needle may be grooved, especially at its tip. Possibly, a spiral is defined on the outside of a needle. It is noted that the finishing and geometry of the outside surface of the needle can affect the direction of advancing of the needle in the bone. In a typical implementation, the needles have a radius of curvature of about 6 mm, a cross-section diameter of between 1 and 1.5 mm and are formed of surgical tool grade stainless steel or implant grade stainless steel. However, smaller sizes are possible, for example a radius of 4 or 3 mm and a diameter or 0.75 or 0.5 mm.

In a preferred embodiment of the invention, the needles are simply pushed into the bone. Alternatively, the needles may be vibrated (axially, trans-axially and/or rotationally, preferably in a reciprocating manner), for example using a piezoelectric motor coupled to them, to aid their advancement into the bone.

In a preferred embodiment of the invention, the needles are advanced and retracted by the action of lever 106 or 206, allowing the boring and threading process to be paced by a physician. Alternatively or additionally, the needles may include a self-retracting mechanism, in which, once the needles bore the hole, they are automatically retraced. This may be achieved using a mechanism similar to that of FIGS. 8D–8F, which is used to couple the needles to their levers. Preferably, the automatic retraction occurs after the thread is treaded through the needles.

In a preferred embodiment of the invention, one of the two needles can be a non-penetrating needle, for example a flat (possibly angled) anvil. Preferably, the anvil includes a hole to receive the other needle. Alternatively or additionally, the anvil also advances when the needle advances. Alternatively, the anvil is fixed. Preferably, the anvil includes small spikes or other gripping elements for engaging the bone so the anvil does not slip and/or to assist in applying a contra-force to stabilize the needle.

Figure 9A:
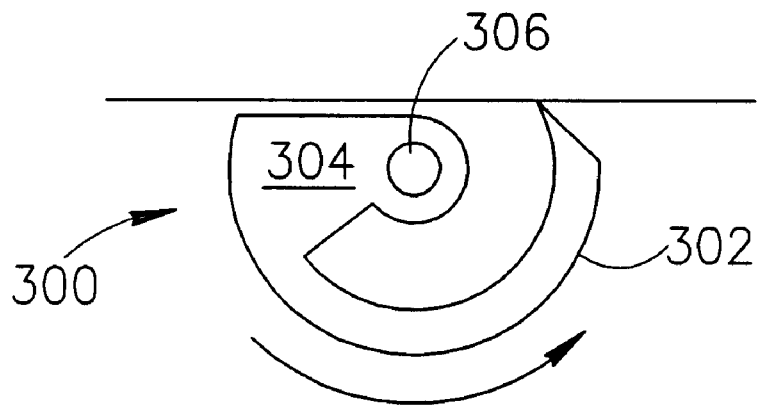
FIGS. 9A and 9B schematically illustrate a hinged single needle boring head, in accordance with a preferred embodiment of the invention.
Figure 9B:
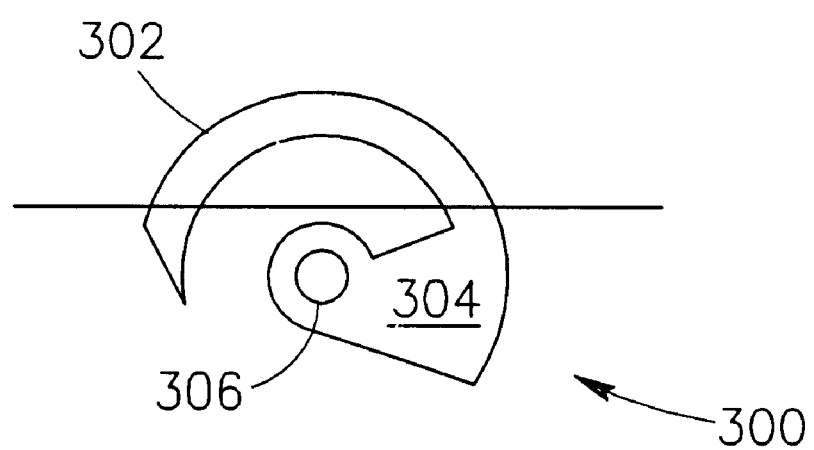

FIGS. 9A and 9B schematically illustrate a hinged single needle boring head 300, without an anvil, in accordance with a preferred embodiment of the invention. Head 300 comprises a needle 302 connected to a hinge 304 via a needle arm-304. In a preferred embodiment of the invention, needle arm 304 also serves as a needle stop to stop the advance of the needle once it completes its path. FIG. 9B shows the single needle when it complete boring through the bone. If needle 302 (or a tip thereof) is detachable from needle arm 304 and is attached to a thread, the tip of needle 302 can be captured by a capture device (not shown), for example by friction, once it exits the bone.

In an alternative embodiment of the invention, the mechanism of FIG. 9 is used for a pair of noodles, to avoid the need for the needle tips to interlock. In a preferred embodiment of the invention, the hole is bored by two needles that meet in the bone. Once the needles meet, their rotation mechanism locks, rather than the needles. Than the rotation of one of the needle is continued over more than 90° (as shown in FIG. 9B for a single needle, for example). Since the mechanism is locked, the other needle is retracted along its bore. Once the advancing needle's tip is outside the bone, it can be engaged by the bone boring device and detached at its base (like needle 282 in FIG. 8D), so that when the bone boring device is retracted, a thread attached to the advancing needle is threaded through the bore in the bone. Preferably, only one of the needles rotates more than 90°, however, based on the geometry, it might be required for both needles to travel at least an angle of 110°, for example. The needle that travels a longer path may be grasped in its middle, at least during the bone boring step, to prevent its distortion. However, this is not essential.

A feature of some preferred embodiments of the invention is an invariance to the angle of incidence between the boring head and the bone. This invariance has several aspects, one or more of which are provided by some preferred embodiments of the invention:

(a) depth of penetration invariance;
(b) slippage invariance; and
(c) bone penetration ability invariance.

Figure 10A:
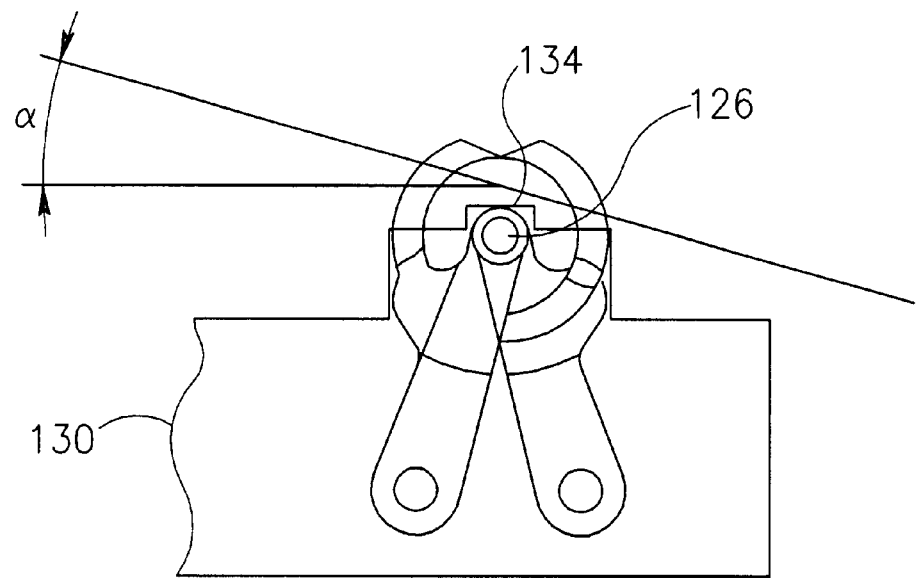
FIG. 10A illustrates an angle independence of a boring head, in accordance with a preferred embodiment of the invention.

FIG. 10A illustrates an angle independence of boring head 130, in accordance with a preferred embodiment of the invention. Due to there being only a small distance between resting point 134 and hinge 126, the penetration depth is unaffected by small, and even some large angles between the resting point and the bone. Since, rotation around the resting point does not substantially affect the distance between the resting point and the meeting point of the needles. In a preferred embodiment of the invention, the small distance is less than 60%, 40%, 20% or 10% of a radius of curvature of a path along which said needles travel. Due to the simultaneous gripping of the bone by two opposing needles, slippage is prevented. Alternatively, resting point 134 allows the needles to penetrate the bone at many different attack angles, even if the needles are not in contact with the bone at a beginning of extension, since resting point is. In some embodiments, the resting points may be roughened or include barbs, to assist in its engaging the bone and/or intervening soft tissue. Alternatively or additionally, the gain for each needle may be different, so they rotate at different speeds and different entry angles are provided.

Figure 10B:
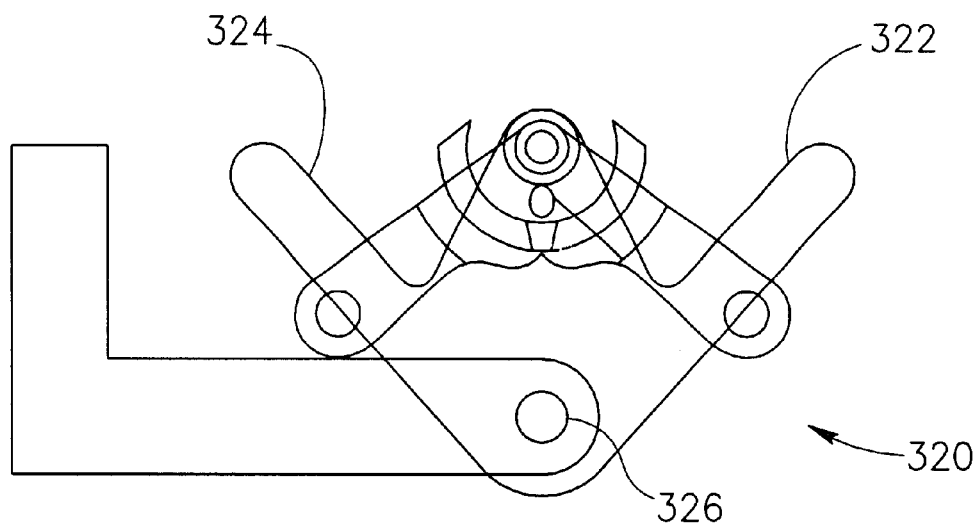
FIG. 10B illustrates a self-aligning boring head, in accordance with a preferred embodiment of the invention.

FIG. 10B illustrates a self-aligning boring head 320, in accordance with a preferred embodiment of the invention. In this embodiment, head 320 is gimbaled on one or more hinges 326, so that head 320 is always facing to the bone, such that both the needles can enter the bone at substantially the same angle and time. In a preferred embodiment of the invention, a pair of stabilizers 322 and 324 contact the bone and straighten head 320. Alternatively to an axial hinge, as shown, an integral hinge may be used, for example one formed of silicon rubber. Possibly, three or more stabilizers are provided, to provide stability also in the plane perpendicular to the needle path. Possibly, the tips of the stabilizers are soft, to prevent inadvertent damage to soft tissue. In an alternative preferred embodiment of the invention, head 320 is self-aligning even without such stabilizers, by the unequal forces against the needles causing the head to gimbal. Alternatively, the mechanism for rotating the needles may only rotate one needle relative to the other. The absolute angular position of the needles is determined by the relative resistance each needle feels.

Alternatively or additionally, to being self-aligning, head 320 can include one or more sensors for determining that the head is in a correct configuration. In one example, a force sensor is provided at each of the stabilizers, to determine a contact force, which should be approximately the same for all the stabilizers. Alternatively or additionally, force sensors are connected to the needles, both of which should measure about equal forces. Possibly, the result of the sensor measurement is portrayed to a user, for example as a go/no-go signal. Alternatively or additionally, the signal from the sensor is used to free a pin, which freeing will allow the extension of the needles. Alternatively, a mechanical construction may be provided, which allows motion of the needles and/or force to be transferred to the needles only if the pressure on the stabilizers and/or their alignment is about the same.

Although the above description of angles has been mainly with respect to an angle in the plane of the needles, similar considerations, measurements and apparatus can be utilized for controlling the angle between the needle plane and the surface of the bone.

Further, the above description has been mainly directed to needles that share a plane or that travel in parallel planes. In some embodiments of the invention, the needles may travel in two oblique planes. An extreme example is cork-screw needles which twist around their own axis (and may be coaxial). Another example is a boring-head comprising three needles, which meet at a point inside the bone. It is noted that the hinge does not need to be at the center of rotation of the needles (if they have one).

Figure 11A:
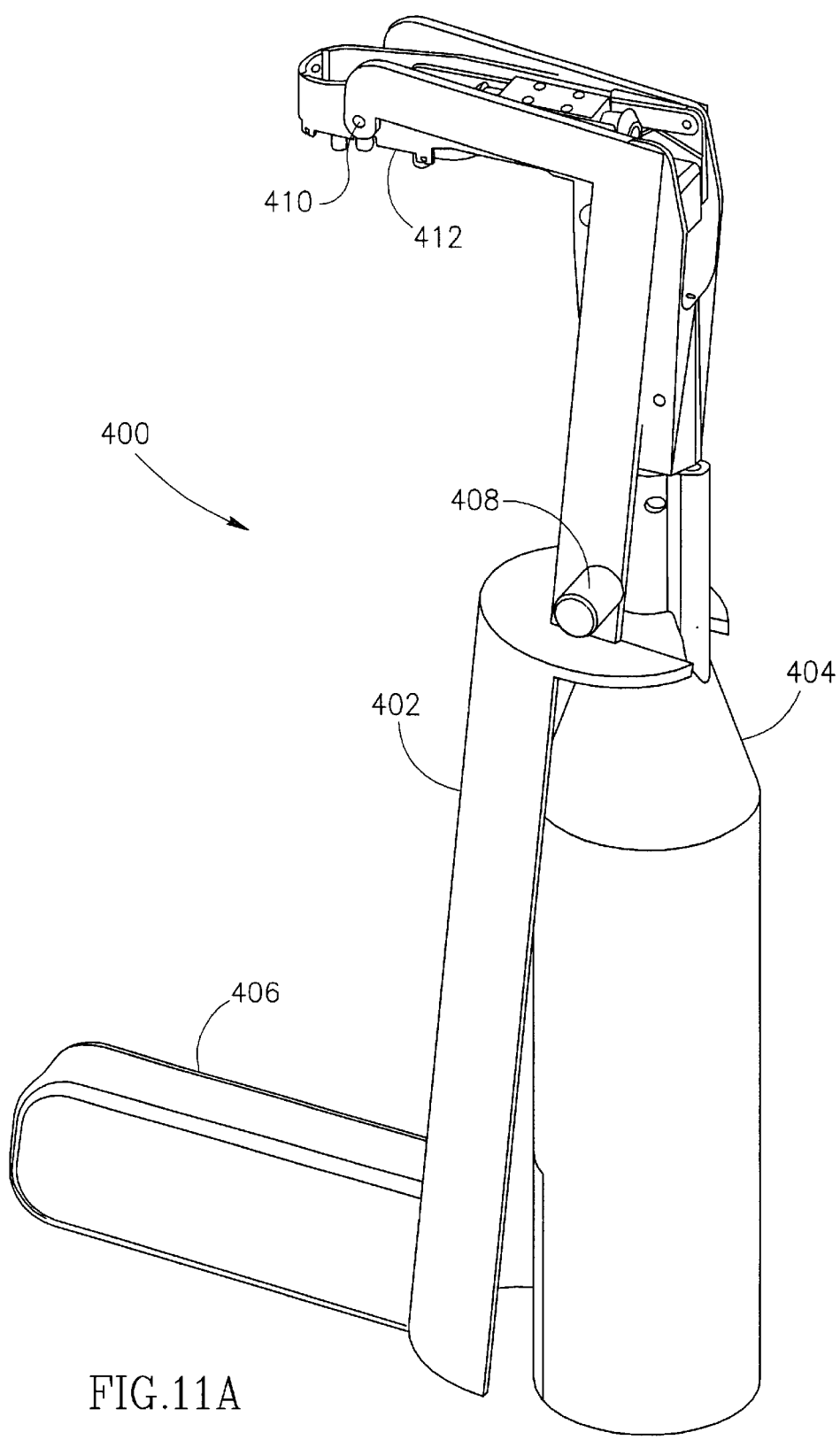
FIGS. 11A and 11B illustrate a self-aligning boring device in accordance with a preferred embodiment of the invention.
Figure 11B:
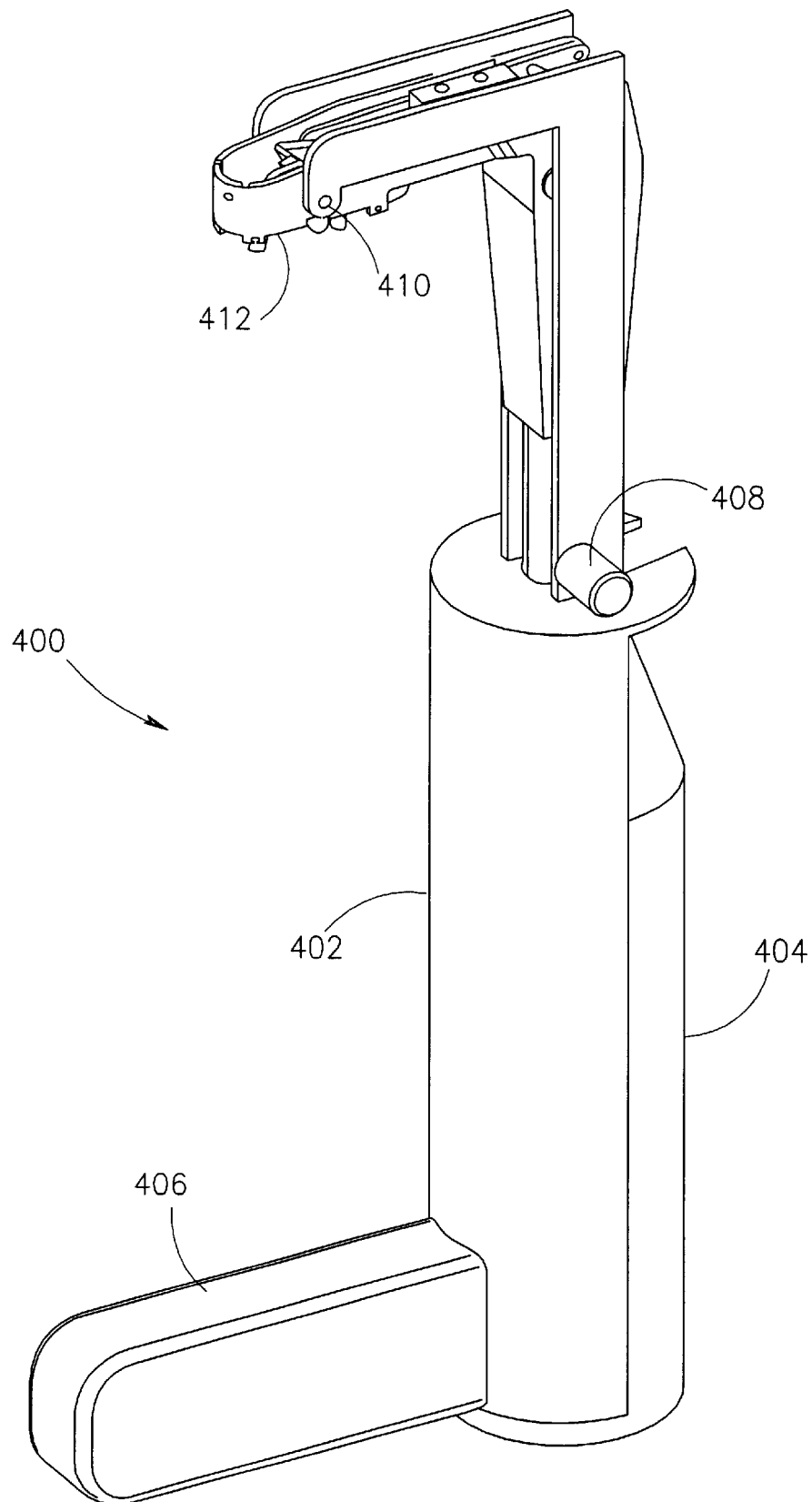

FIGS. 11A and 11B illustrate a self-aligning boring device 400 in accordance with a preferred embodiment of the invention. Device 400 comprises generally of a holder 402 and a boring mechanism 404 and a boring head 412 which is held against a bone by force applied by a user to a handle 406. In an exemplary embodiment, mechanism 404 includes a power source such as a motor and head 412 includes drill bits powered by the motor. A hinge 410 is preferably provided between holder 402 and mechanism 404, preferably near boring head 412, to allow boring head 412 to align itself with the surface of the bone to be bored into, substantially independently of the force vector applied to handle 406. A second hinge 408, preferably with a positional freedom of motion, may be provided to maintain the relative positions of holder 402 and mechanism 404 and/or as a safety feature to prevent warping of head 412 by undue forces. Alternatively or additionally, reference 408 may represent a safety catch which prevents the extension of the needles until released.

FIG. 11B is a different view of device 400 and showing a relative rotation of holder 402 and mechanism 404 around hinge 410.

In a preferred embodiment of the invention, the hinge is substantially equidistant from the tips of the drill bit, so that a substantially equal force is applied to them. The hinge may be positioned not equidistant, for example, if an unequal force on the two drill bits is desired. Alternatively or additionally, such an unequal force can be provided using a spring which resist the gimbaling of the head. The hinge may be in the head or in the body, for example.

In some embodiments, holder 402 is used as an outer skeleton for an existing mechanism 404, which mechanism can also be used without holder 402. Alternatively or additionally, a holder-type device may be used for other uses than boring holes in bones, for example for stapling and/or tacking in the vagina or the throat.

Figure 11C:
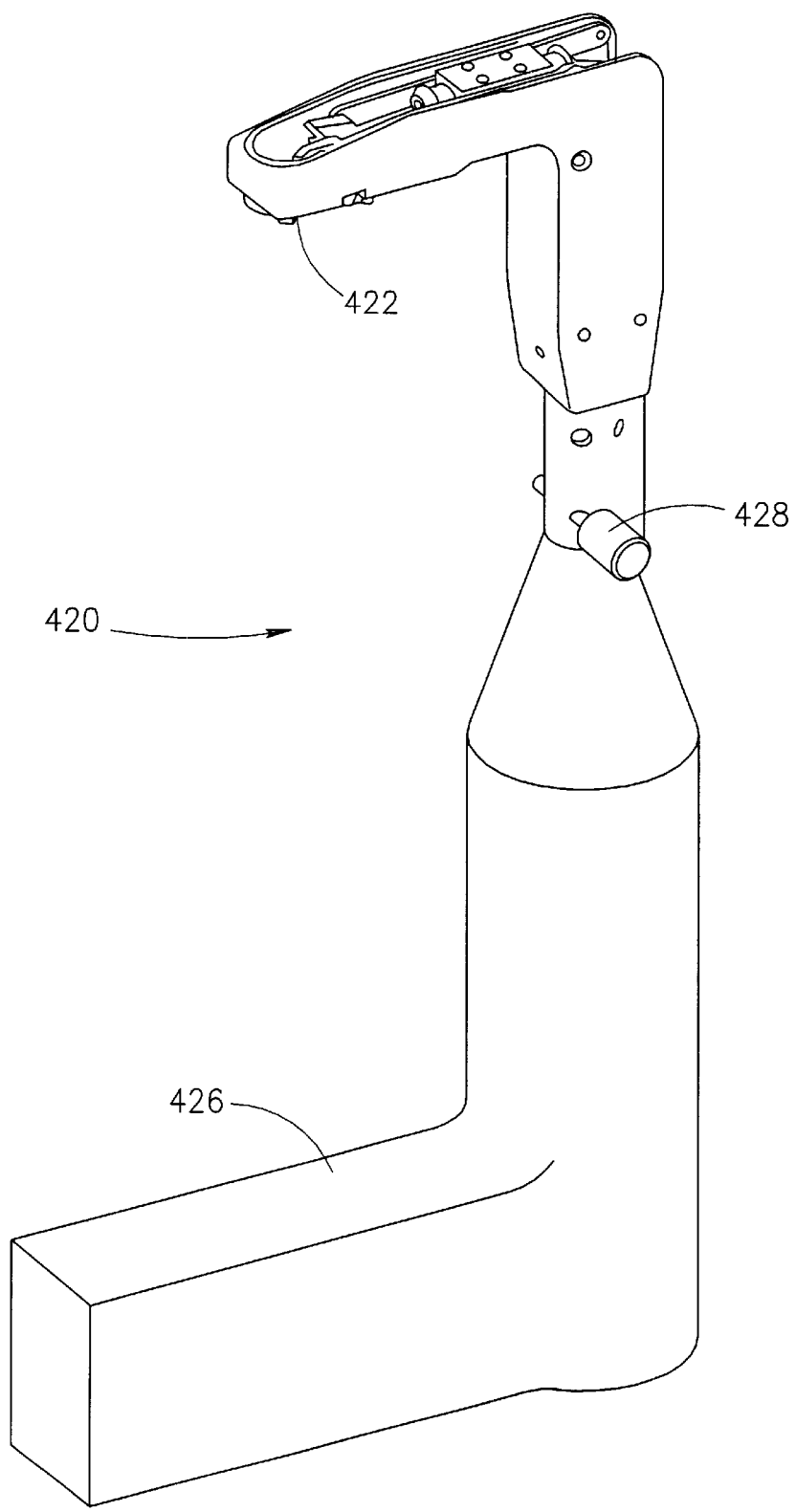
FIG. 11C illustrates an alternative self-aligning boring device, in accordance with a preferred embodiment of the invention.

FIG. 11C illustrates an alternative self-aligning boring device 420, in accordance with a preferred embodiment of the invention. In device 420, a boring head 422 rotates around a hinge 428 which is between a handle 426 and boring head 422. In some embodiments, the angular freedom of hinge 428 is small, for example 5°, 10° or 20°.

In various preferred embodiments of the invention, the path bored in the bone can be threaded in different ways. In a first way, a thread is pulled through the path by one of the needles. In another way, the thread is pushed through the path. In yet another way, a separate threaded needle is brought through the path. One the path is threaded, the ends of the suture are tied together, preferably manually. Alternatively, a clip is attached to the two ends of the thread and performs the functions of a knot. In the case where the device performs the threading, when the device is retracted from the one, the thread remains in the bone. The suture may be tied immediately. In some cases, some or all the required bone bores are formed first and the threaded and/or tying of sutures is performed later.

A general process of bone suturing, in accordance with some preferred embodiments of the invention thus comprises:

(a) compressing soft tissue against the bone (optional);
(b) advancing needles through the soft tissue and the bone, to bore a path through the bone;
(c) advancing a thread along the path, preferably while the needles are still in the hole (or by the advance of the needles);
(d) removing the device (generally first retracting the needles); and
(e) tying the ends of the thread.

In various embodiments of the invention, selected ones of these steps may be performed sequentially or simultaneously. Even in cases when sequential steps arm performed, the transition between the steps may be automatic, for example advancing a thread one the needles are filly extended, or manual, for example requiring a user action (manually advancing a thread) or allowance (releasing a safety latch).

As indicated above, a thread may be pushed through the bores of the needles, after they meet. Generally, pushing a thread will require the thread itself to be stiff or to be attached to a stiff thread pusher, which is pushed and carries the ductile thread along with it. The stiffness of the thread/thread pusher depends, inter alia, on the radius of the bore, the amount of bone material in the bore and the type of mechanism used to advance the thread.

Figures 12A, 12B:
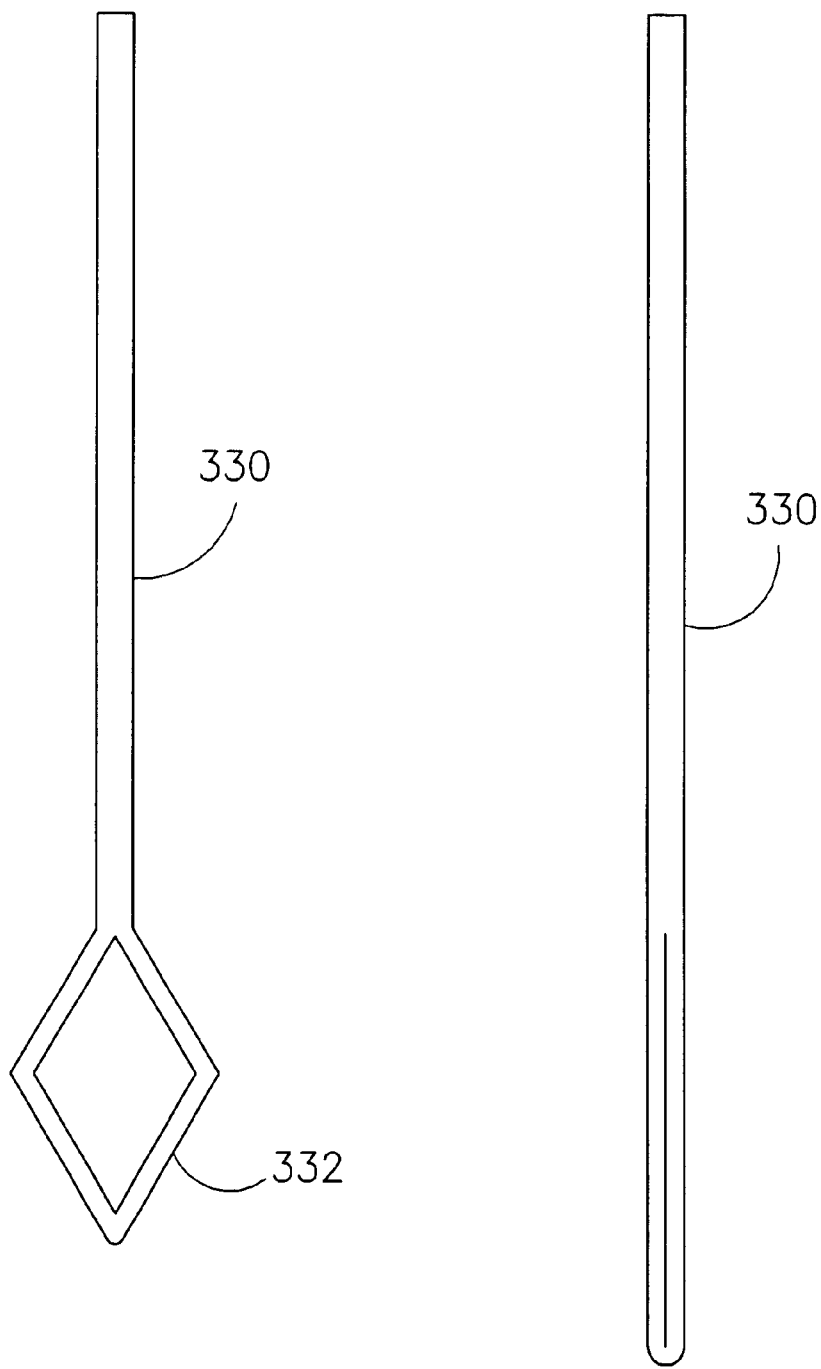
FIGS. 12A and 12B illustrate a thread pusher, in accordance with a preferred embodiment of the invention in an open configuration and in a closed configuration.

FIGS. 12A and 12B illustrate a thread pusher 330, in accordance with a preferred embodiment of the invention in an open configuration and in a closed configuration. In a preferred embodiment of the invention, pusher 330 is formed of an elastic or super elastic material and has an eye 332 formed at one end thereof. A thread is threaded through the eye and then the thread pusher is inserted into a channel (or the needle bore). The dimensions of the channel compress the eye, so that it grips the thread. Alternatively, a double thread may be used, so that both ends of the thread are far away from the eye.

Figure 13A:
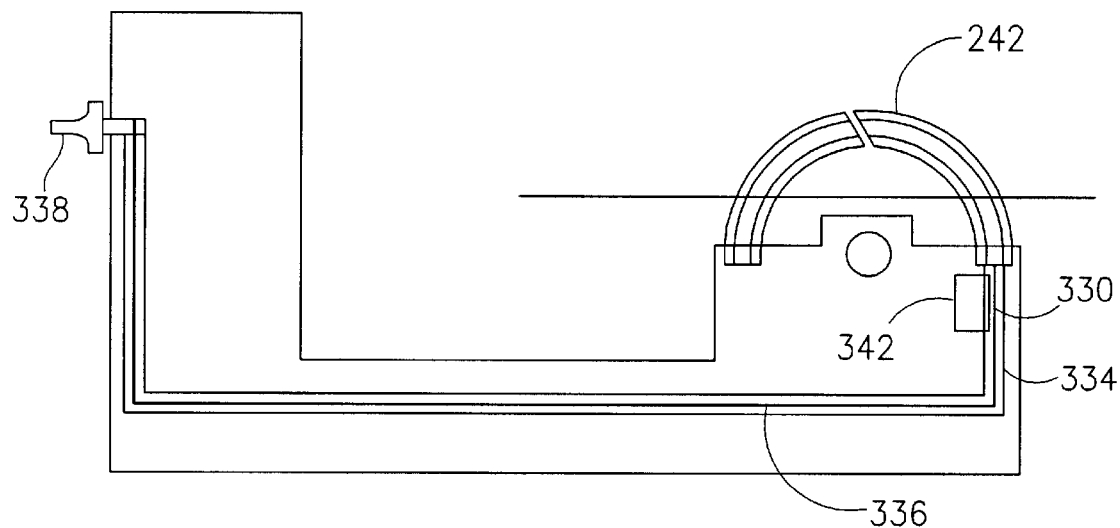
FIGS. 13A and 13B illustrate a method of passing a thread through the bores of the needles of FIGS. 5A and 5B, in accordance with a preferred embodiment of the invention.
Figure 13B:
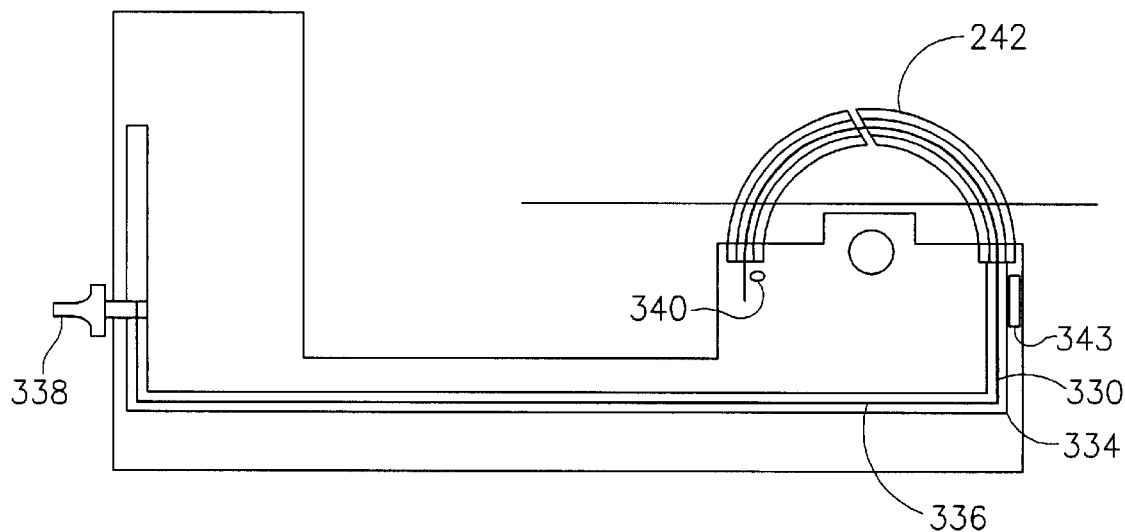

FIGS. 13A and 13B illustrate a method of passing a thread through the bores of the needles of FIGS. 5A and 5B, in accordance with a preferred embodiment of the invention. A channel 334 contains thread pusher 330. A lever 338 is coupled to thread pusher 330, such that moving the lever advances the thread pusher. Depending on the configuration used, reference number 336 may indicate an extension of thread pusher 330 or a thread attached to thread pusher 330.

In FIG. 13A, the needles meet, but lever 338 maintains the thread outside the needle bore. In FIG. 13B, the lever is depressed and the thread is advanced through the needle bore. Optionally, an engager 340, possibly a friction element, engages read pusher 330 and/or the thread, so that it does not retract when the needles are retracted and/or when the device is removed from the bone. In embodiments where the needles retract automatically when the bore is threaded, engager 340 may also release a catch on a spring that retracts the needles.

In one embodiment of the invention, thread pusher 330 is urged forward by a spring 342 (shown schematically). However, advance of pusher 330 is prevented by lever 338. In other embodiments, a pin, such as shown in FIGS. 8D–8F, prevents the thread pusher from entering the needle bore, even if it is urged forward by a spring. Preferably, the tip of thread pusher 330 is preloaded into the tip of needle 242, so that it travels with the needle. Alternatively, channel 334 is arranged so that it has a clear view of the bore only when the needle is fully extended.

In some embodiments, bar 232 and/or bar 230 (shown in FIG. 4), when they completely extend the needles, continue their travel (preferably sliding along anchors 140 and 142) and are used to retract the thread pusher and/or to advance it.

Figure 14A:
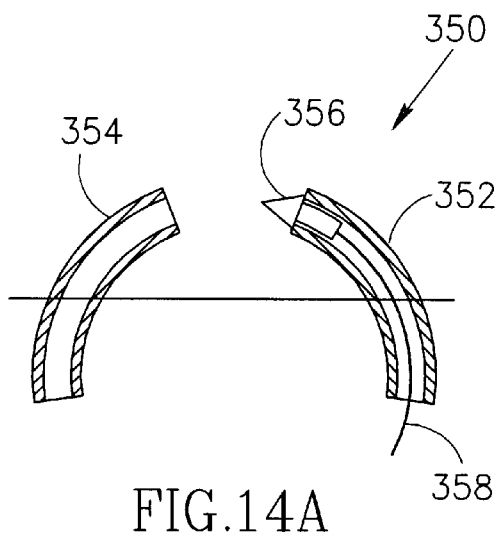
FIGS. 14A–14D illustrate various stages in a usage of a thread-exchanging needle assembly, in accordance with a preferred embodiment of the invention.
Figure 14B:
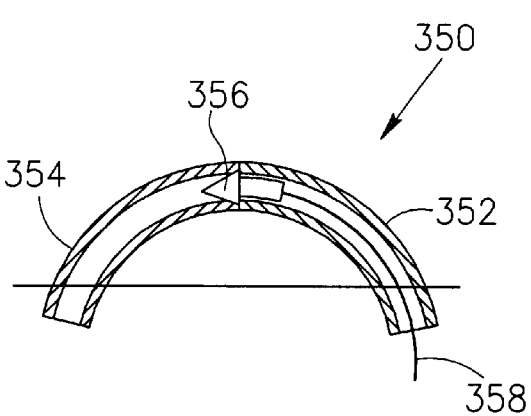
Figure 14C:
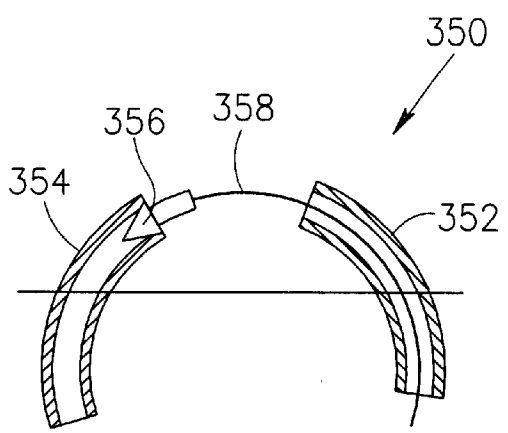
Figure 14D:
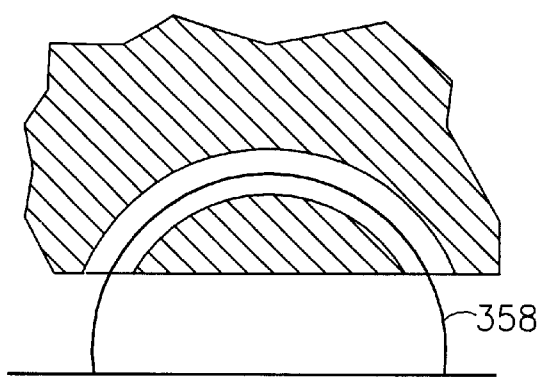

FIGS. 14A–14D illustrate various stages in usage of a thread-exchanging needle assembly 350, in accordance with a preferred embodiment of the invention. Assembly 350 preferably comprises a needle 352, a needle 354, a tip 356 mounted on needle 350 and attached to a thread 358. The tips of needles 352 and 354 are formed to engage tip 356 in the following manner. Tip 356 is preferably frictionally engaged by needle 352 so that it does not fall off (FIG. 14A). Whenever two needles are brought together, the point of tip 356 is engaged by an inner bore (or other spatial configuration) of needle 354 (FIG. 14B). When the needles are acted (FIG. 14C), the engagement of the tip by needle 354 is stronger than was the engagement by needle 356, so that the tip travels with needle 354. When the device is removed, thread 358 remains in the bore (FIG. 14D). In some embodiments of the invention, needle 354 is replaced by an anvil (which does not enter the bone) or by a tip-engager that is distanced from the bone, but is within the needle track.

Figure 14E:
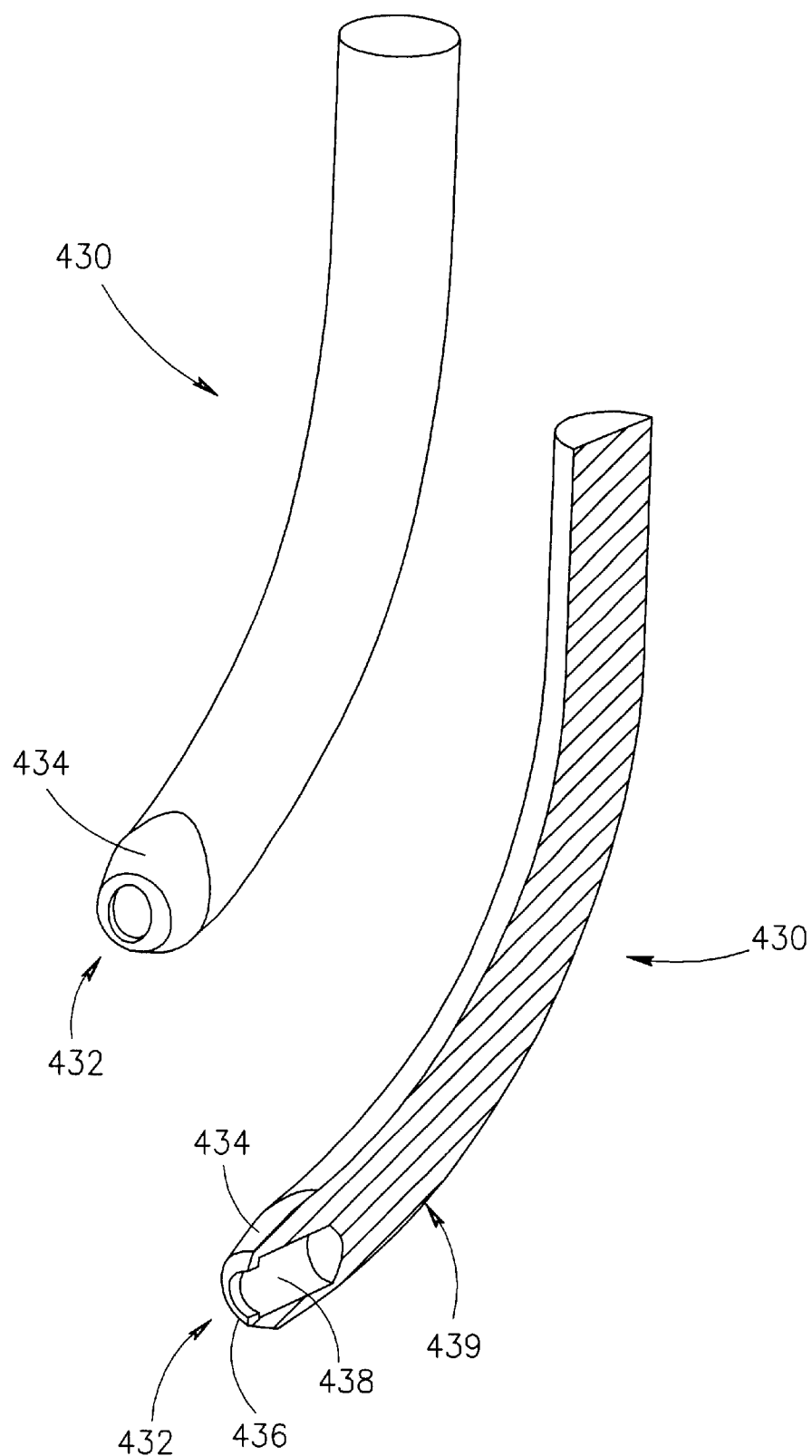
FIGS. 14E–14H illustrate needle-receiving tips in accordance with various preferred embodiments of the invention.

FIGS. 14E–14H illustrate needle- (or needle-tip) receiving tips in accordance with various preferred embodiments of the invention. For clarity of presentation, all these figures include a perspective view and a corresponding perspective axial cross-sectional view. FIG. 14E illustrates a needle 430, having an aperture 432 formed at its tip. An inner volume 438 is hollowed out in the needle. Preferably, but not necessarily, an outer lip 436 of the aperture has a smaller diameter than that of volume 438. Lip 436 is preferably smooth, however, this is not essential and lip 436 may be, for example, jagged. Optionally, an incline 434 is defined adjacent aperture 432, to bridge the outer diameters of needle 430 and lip 436.

Optionally, volume 438 is longer than shown and exits the side of needle 438 at a location marked 439. Thus, any bone material that enters volume 438 can be pressed out by the received tip of the opposite needle.

Figure 14F:
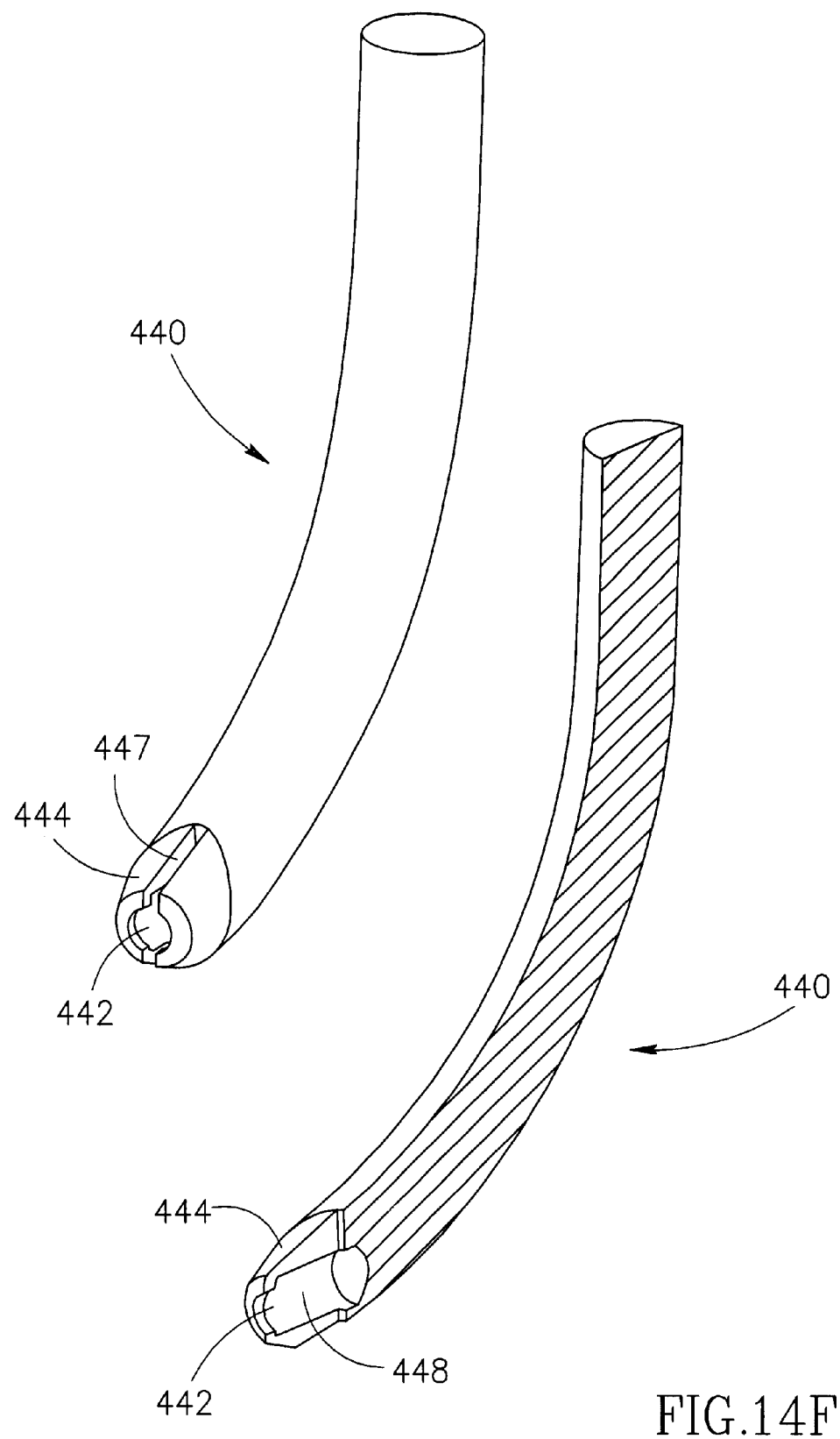

FIG. 14F illustrates an aperture 442 for a needle 440, similar to the design shown in FIG. 14E, except that one or more slots 447 are formed between a volume 448 defined in the needle and an incline 444 on the outside of the needle. Slot 447 can server to exhaust debris from volume 448 and/or for adding elasticity to aperture 442, for assisting in engaging the tip of the opposite needle.

Figure 14G:
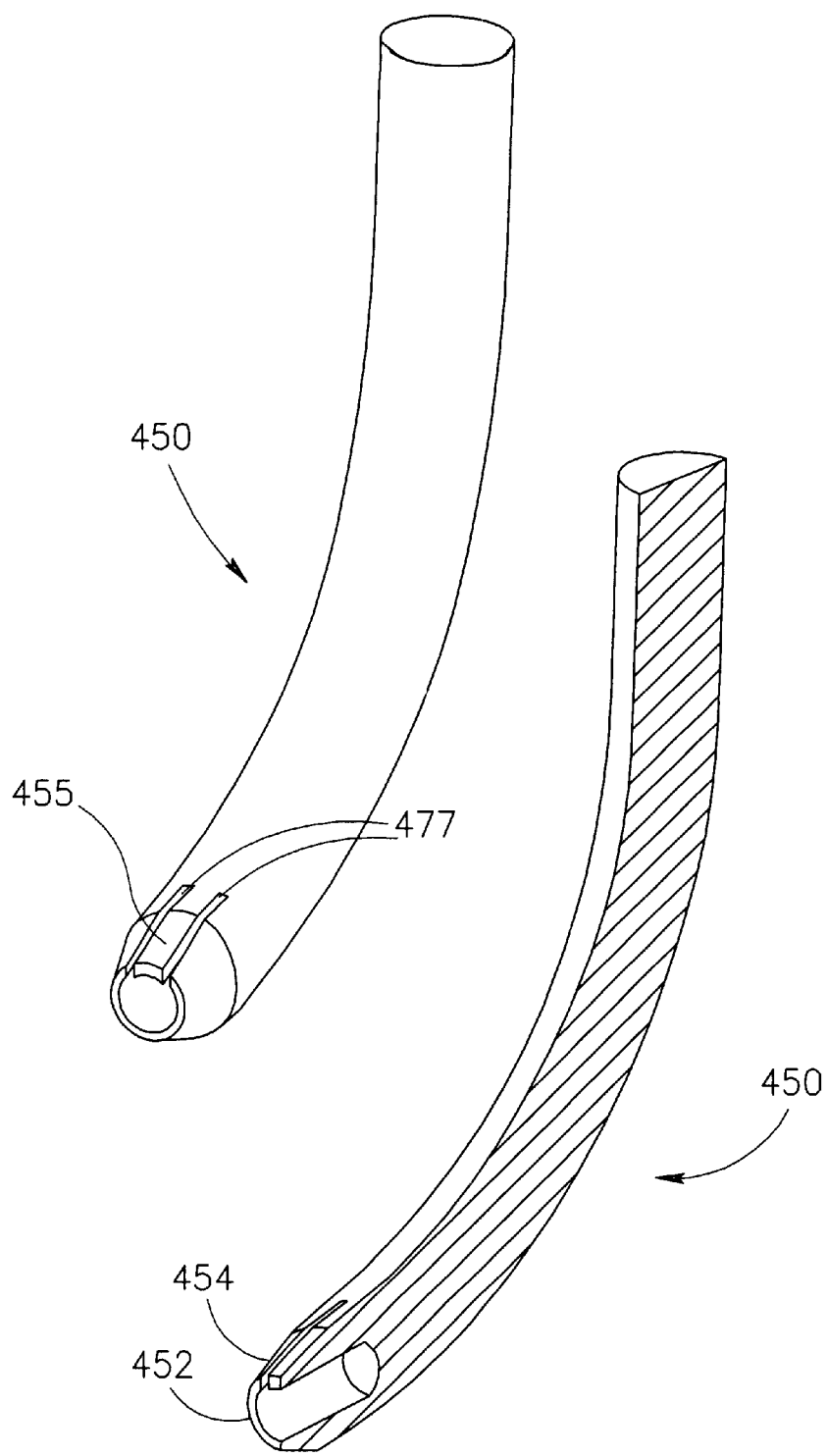

FIG. 14G illustrates a needle tip design similar to that of FIG. 14F, except that two slots 457 are defined between a volume 458 in a needle 450 and an incline portion 454 of the needle. The two slots are nearby, defining a flexible tab 455 between them. Tab 455 can, for example, provided an elasticity or plasticity in an aperture 452, to engage the other needle tip.

Figure 14H:
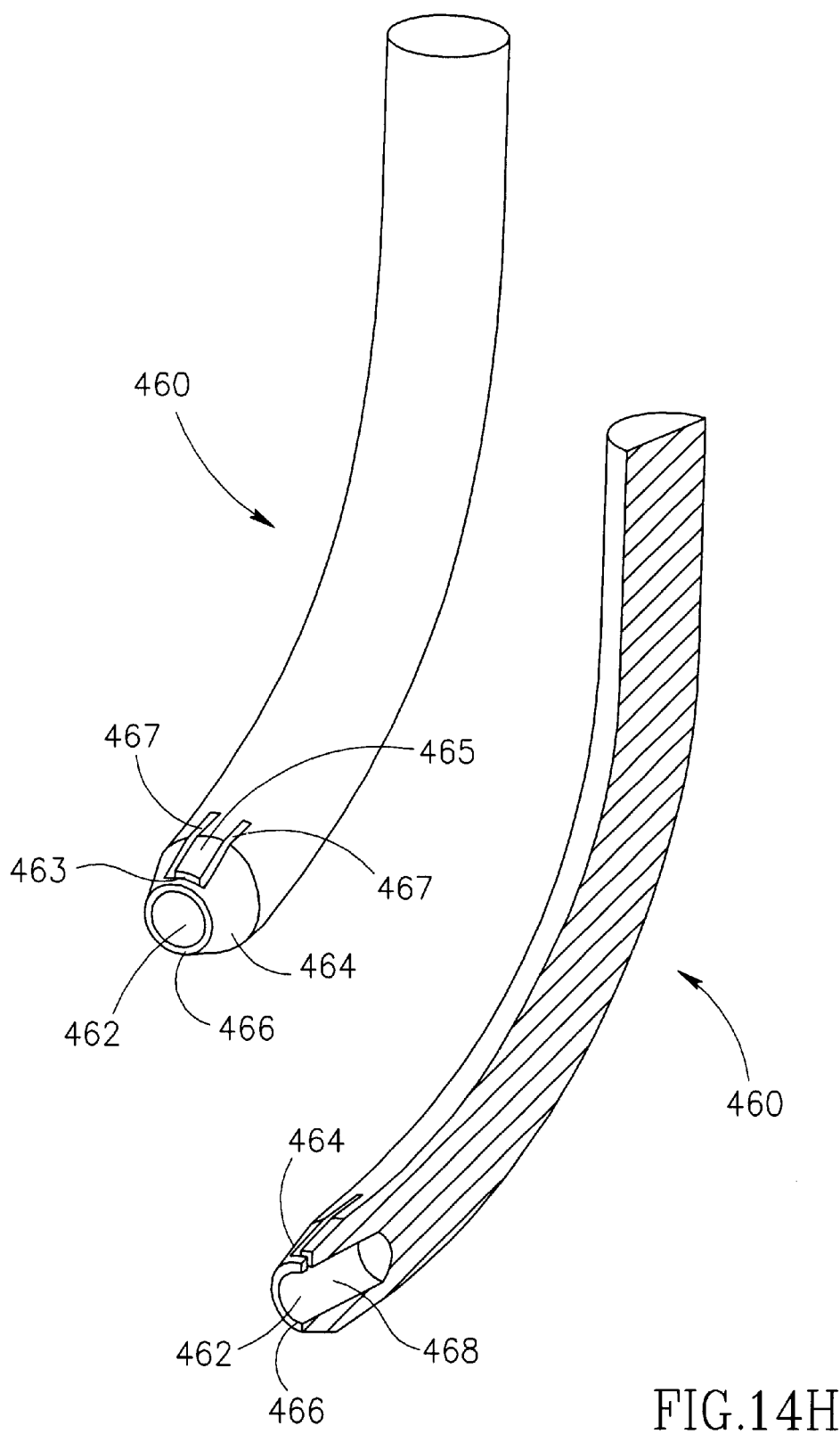

FIG. 14H illustrates a variant of the design of FIG. 14G, in which a pair of slots 467 do not extent to a lip 462 of an aperture 466 defined in a needle 460. Rather, a small slot 463 bridges between the ends of slots 467, so that a tab 465 is formed. Lip 462 is thus whole and tab 465 is less likely to be distorted by the travel in the bone than is the design of FIG. 14G.

FIGS. 15A–18D illustrates a hollow needle boring mechanism, in accordance with a preferred embodiment of the invention, in which a bore in one of the needles is filled by a reacting mandrel.

Figure 15A:
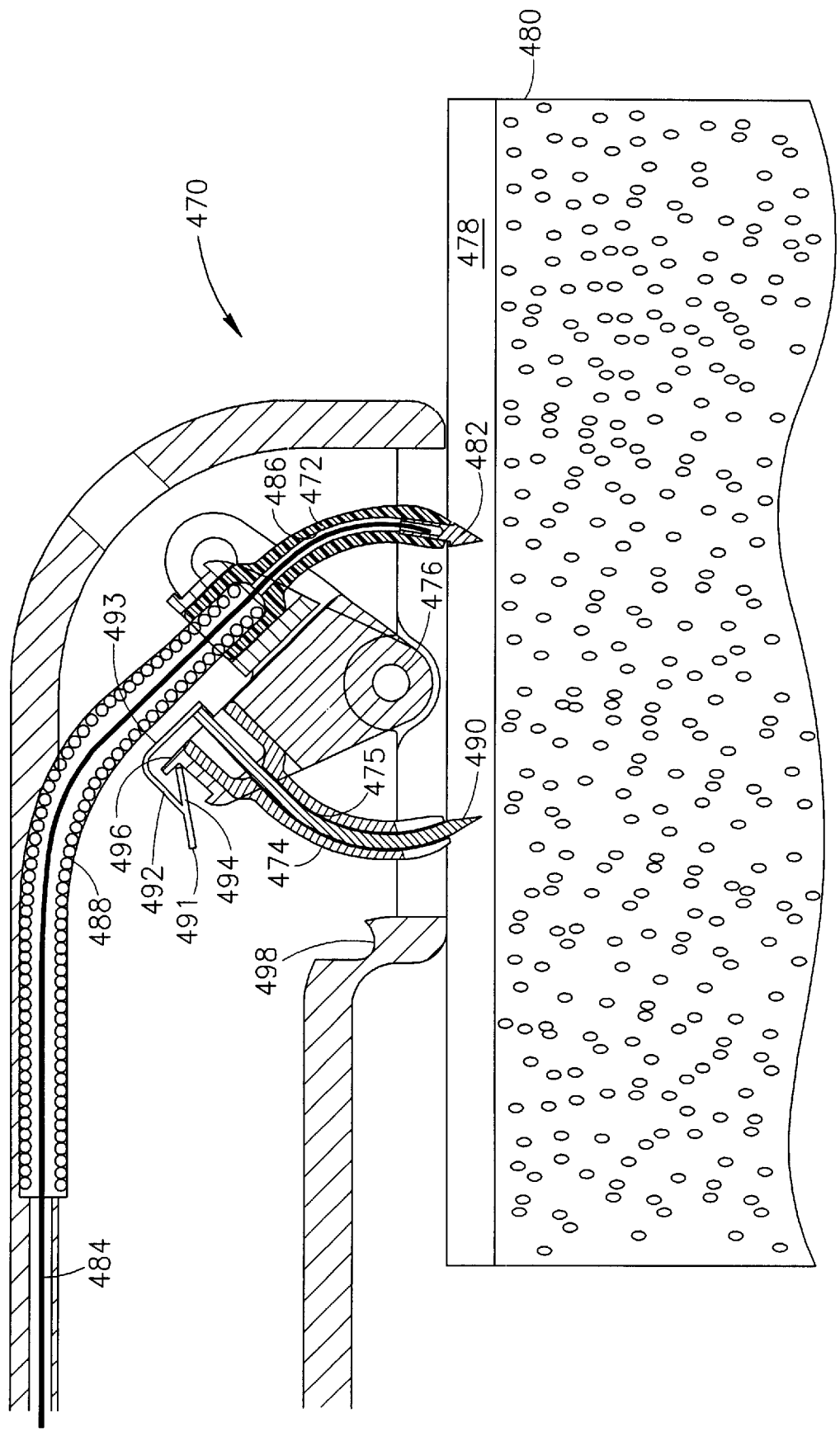
FIGS. 15A–15D illustrates the operation of a hollow needle boring mechanism, in accordance with a preferred embodiment of the invention, in which a bore in one of the needles is filled by a retractable mandrel.

FIG. 15A illustrates a needle-boring head 470, having two opposing hollow needles, a needle 472 which carries a tip 482 and a tip-receiving needle 474. In some embodiments, needle 472 is not hollow, for example as described above. The two needles preferably rotate around a hinge 476. Tip 482 is preferably attached to a thread 484, which can be carried past a bore 486 of needle 472, to a conduit 488, preferably an elastic conduit, for example an axially flexible conduit. A mandrel 490 is preferably provided in a bore 475 of needle 474. Mandrel 490 is preferably maintained in an axial position relative to needle 474 for example by a stop-clip 492. Stop clip 492 preferably includes a base 493 against which mandrel 490 is placed, an arm 494 which engages a protrusion 496 of needle 474, so that stop-clip— 492 holds mandrel 490 in place. Stop clip 492 preferably also includes an extension 491, adapted to match a protrusion 498 in head 470, for releasing stop-clip 492.

FIG. 15A shows mandrel 490 and tip 482 forced into or against a cortex layer 478 of a bone and overlaying a medulla 480 of the bone. The tissue may be removed or is not shown for clarity of presentation.

Figure 15B:
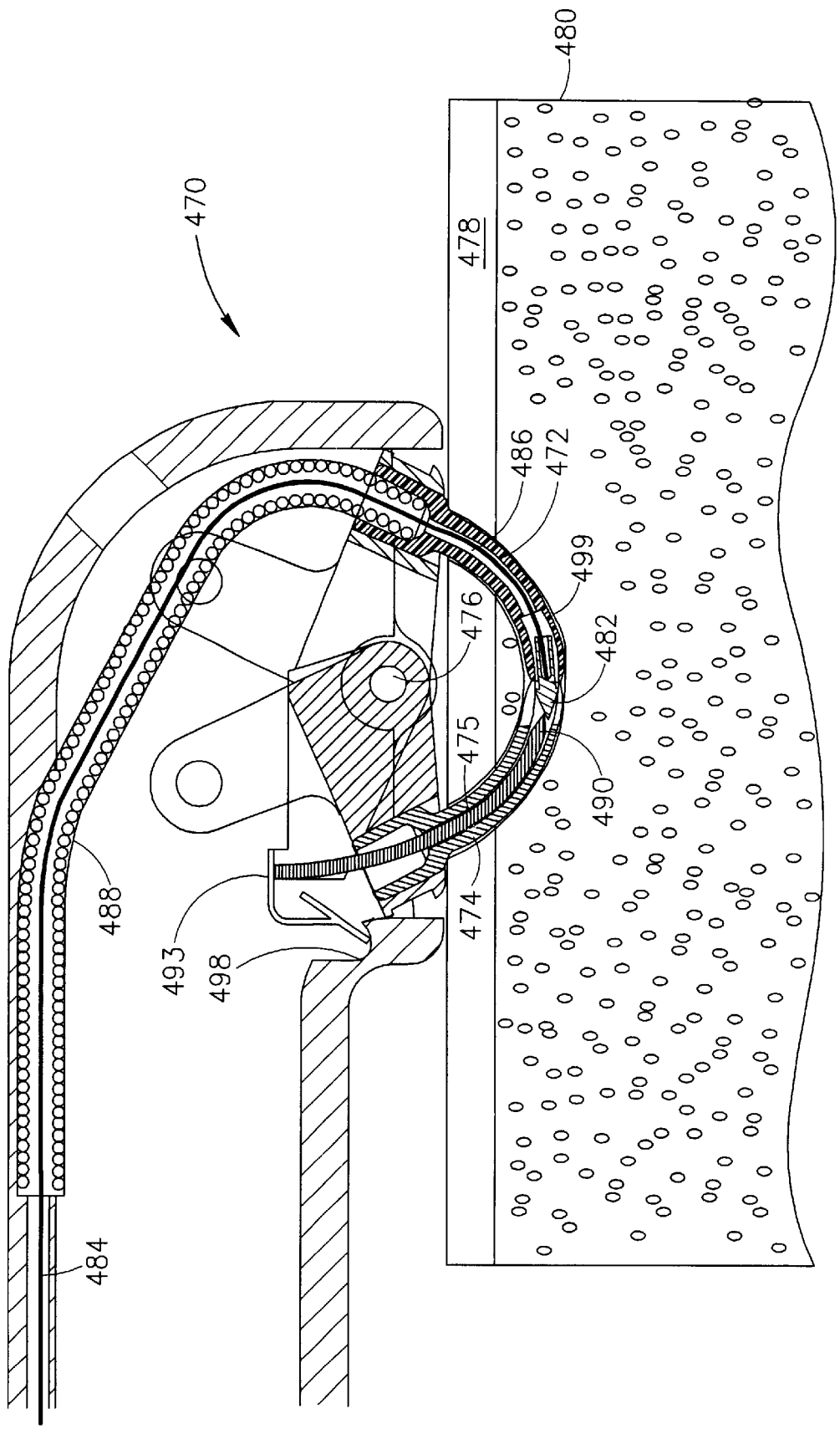

In FIG. 15B the needles are rotated around hinge 476, so they create a bore 499 through cortex 478 and medulla 480. During the advance of needle 474, extension 491 is stopped by protrusion 498, causing stop-clip 492 to disengage from needle 474 and allowing mandrel 490 to retract. Thus, an aperture appears in the tip of needle 474, into which tip 482 can enter and by which it can be engaged. Preferably, the tip of needle 474 is slotted, for example as described with reference to FIGS. 14F–14G. In a preferred embodiment of the invention, bore 475 is filled with debris from medulla 480, as mandrel 490 retracts, preventing the formed aperture from being blocked.

Figure 15C:
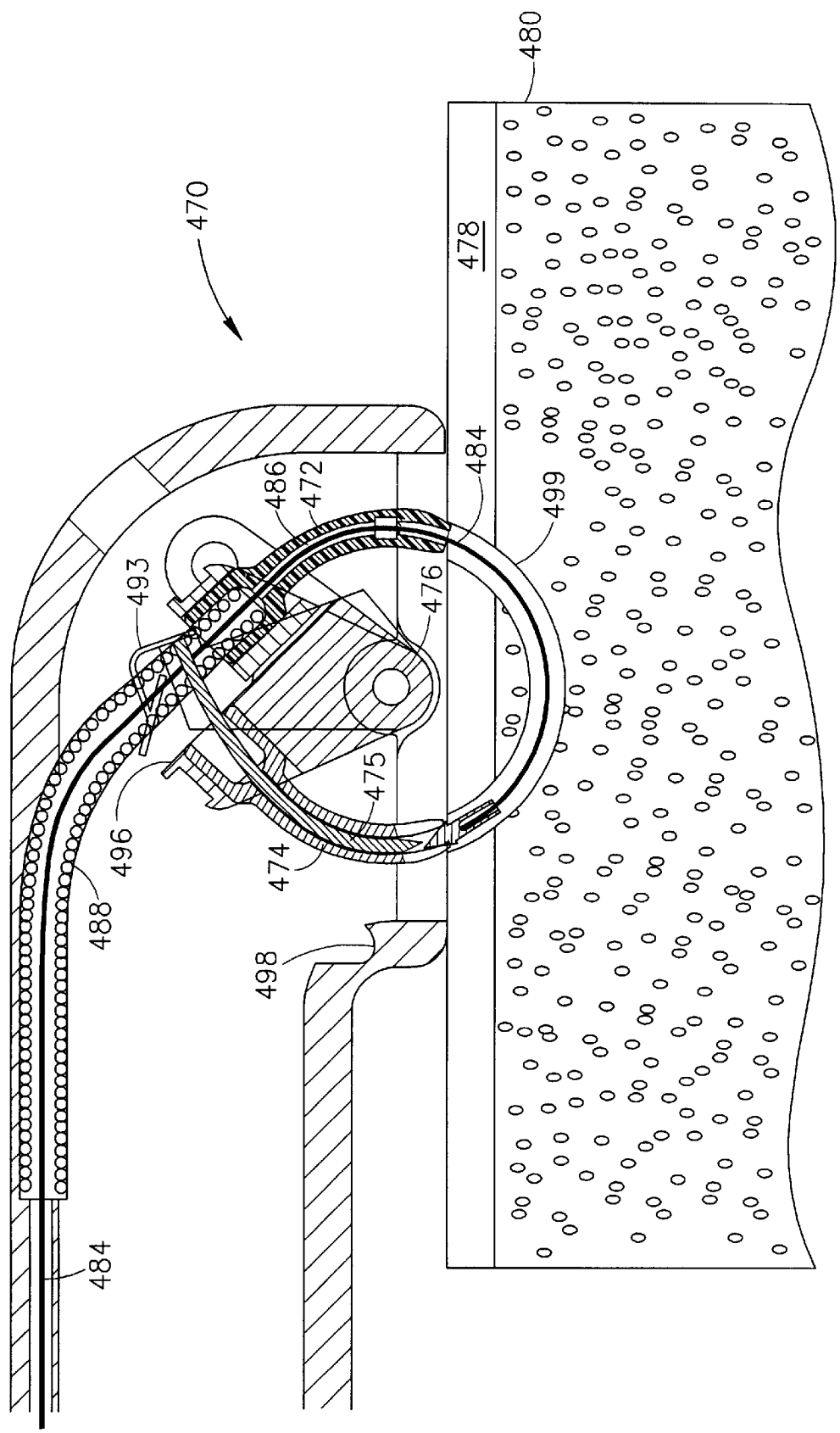

In FIG. 15C, the needles are retracted, so thread 484 enters bore 499.

Figure 15D:
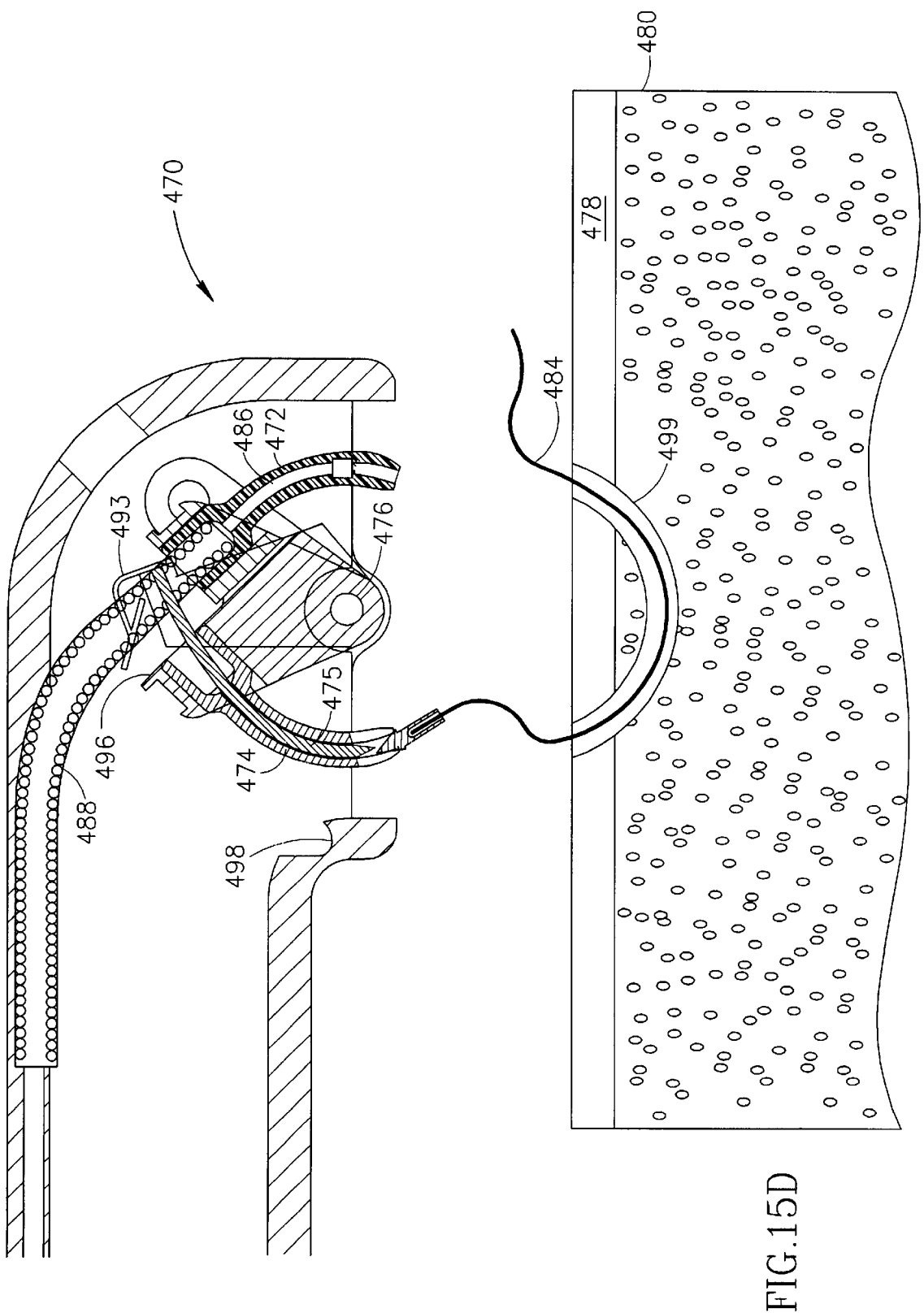

In FIG. 15D, boring head 470 is separated from the bone, leaving thread 484 threaded through bore 499.

In some embodiments of the invention, what is shown as a thread 484 is actually a metallic extension of tip 482, for example made of Nitinol, to which a thread may be connected. Thus, the thread is far away from tip 482 and is not near the bone during the boring procedure. It is noted that a hollow needle with a mandrel may also be used for a single needle device, such as shown in FIGS. 9, for example to assist in engaging the needle when it finishes its travel.

Figure 16A:
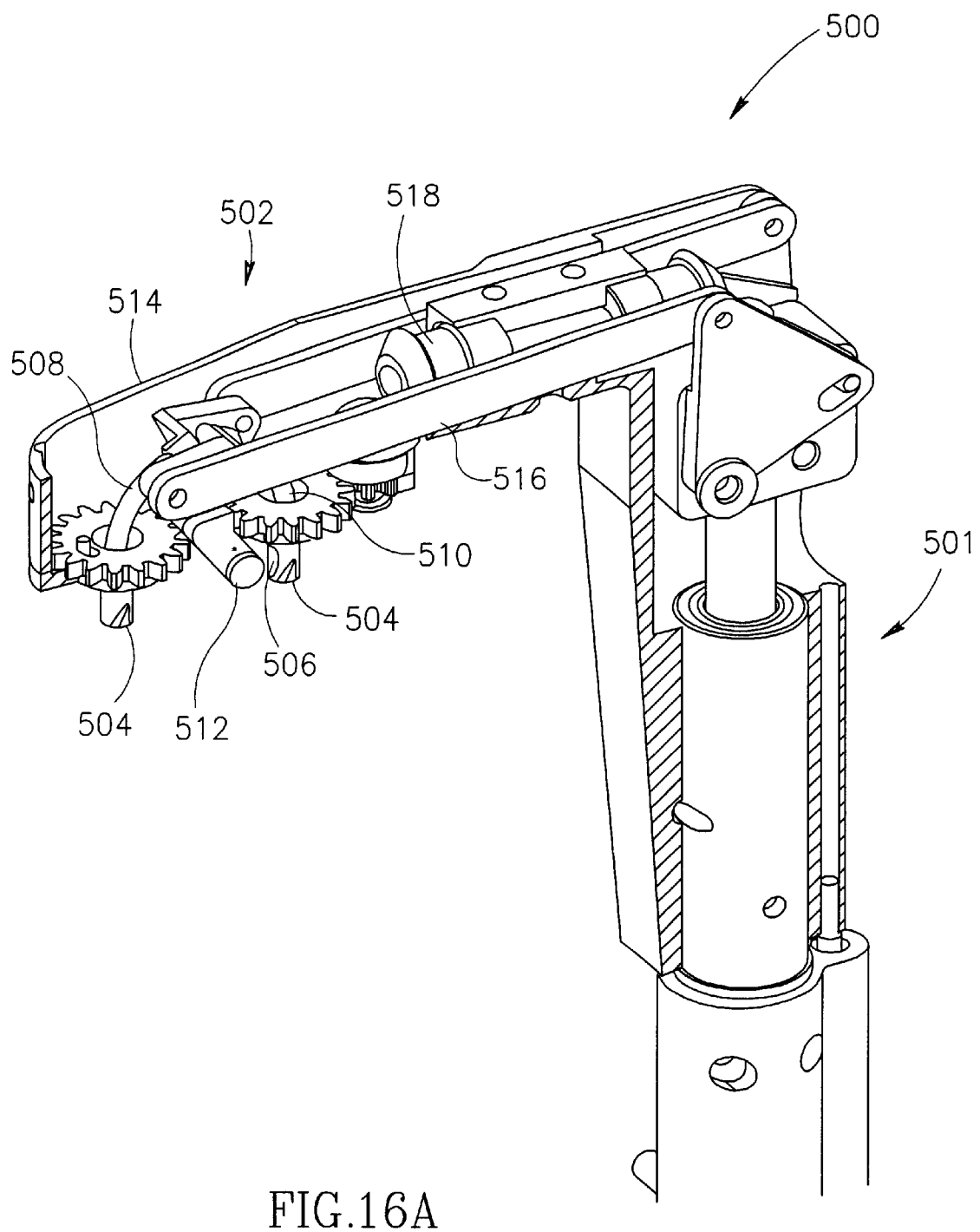

FIGS. 16A and 16B illustrate a combination drilling and needle boring head, in accordance with a preferred embodiment of the invention. A combined drilling and boring device 500 preferably comprises a combination drilling and boring head 502 attached to a handle 501. FIG. 16A shows device 500 with the needles retracted and FIG. 16B shows the device with the needles extended. As shown in FIG. 16A, two drill bits 504 are provided, each with one or more openings 506 in its side for passage of one of a needle 508 and a needle 510. The needles may share a single hinge, or as shown in the Figure, a hinge 512 may be provided for each needle, coupling the respective needles to a casing 514 of head 502. Various lever types may be used for leveraging the extension of the needles. A power train 516 is shown for advancing the needles. A power train 518 is shown for rotating the drill bits.

FIG. 16B shows head 502 with the boring needles extended, and also affords a better view of the drive mechanism for rotating the drill bits. Although -an exemplary drive mechanism is shown, many other mechanisms can be used within the scope of the invention. The rotation of drive train 518 is preferably transferred to a flat gear 520, which rotates a gear 522 that has a drill bit at its center. A second gear 524 transfers power from gear 522 to a gear 526 that also has a drill bit at its center. In some embodiments, only one drill is used, possibly with a single needle extending through that drill bit. A peg 528 is shown which allows some rotational freedom of the drill bits, so that the needles can be more easily aligned with openings 506.

In an alternative preferred embodiment, the position of peg 528 is detected using a sensor (not shown), which sensor electrically or mechanically stops the rotation of the drill bits, so they will be correctly aligned. Exemplary suitable sensors are optical and magnetic sensors. Alternatively or additionally, a rotational encoder is used to detect the drill bit position. The rotation may be stopped at any point between the motor and the drill bit, depending on the implementation. Alternatively, the motor may be controlled to generate complete rotations, so that the end-position of the drill-bit can be as desired.

In a preferred embodiment of the invention, the two drill bits rotate in a same direction and at a same speed. Alternatively, they may rotate in opposite directions and/or at different speeds. Alternatively, they may have reciprocating motion, rather than pure rotational motion. In some cases, axial or transaxial vibration may also be provided. Optionally, a spike is provided between the drill bits, for maintaining the bits in place before they penetrate the bone. This spike is preferably retracted as the bits advance.

FIGS. 17A–17E illustrate a method of using device 500. Some of the elements of head 502 are not shown, for clarity of presentation.

Figure 17A:
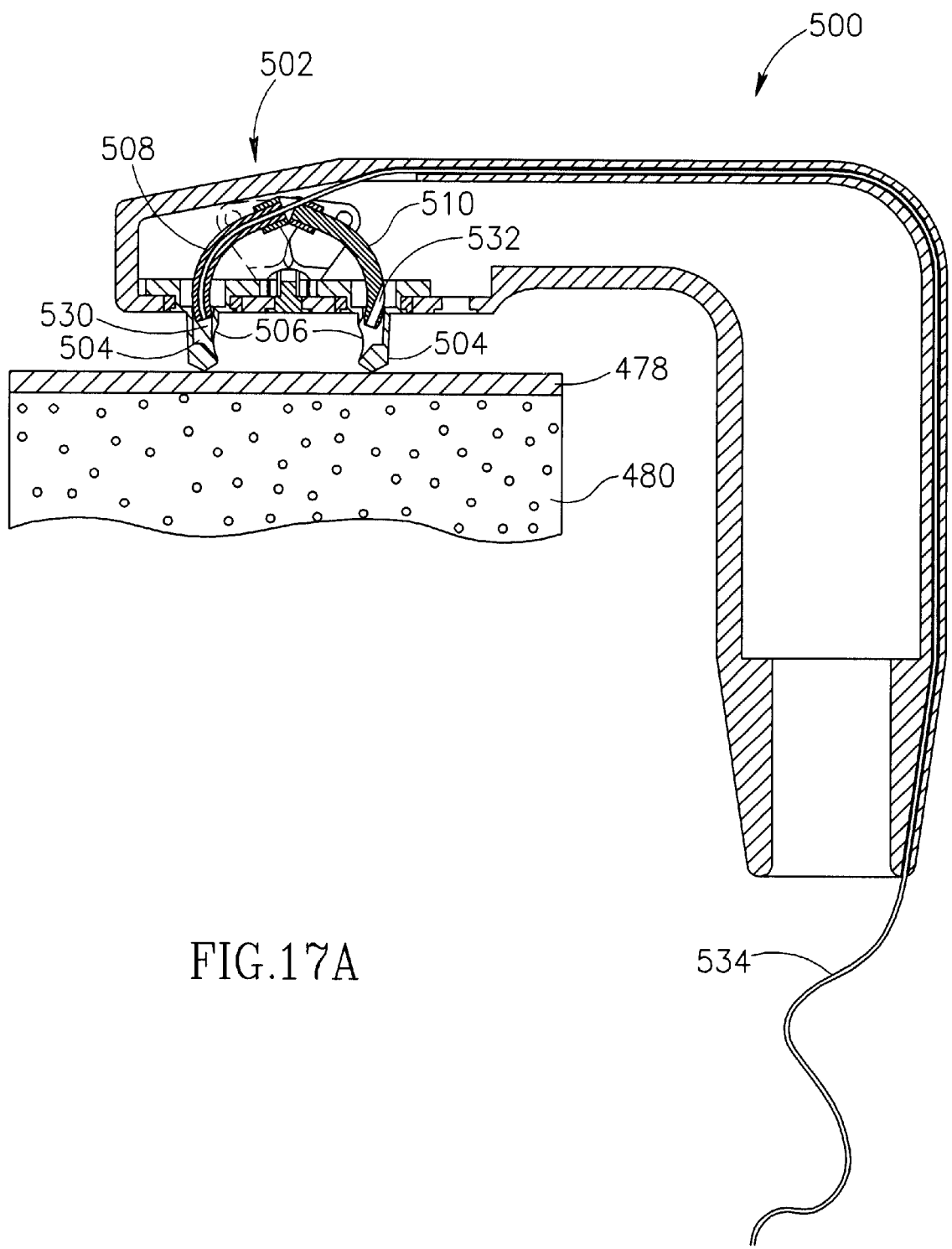
FIGS. 17A–17E illustrate a method of using the combined head of FIGS. 16A–B.

In FIG. 17A, drill bits 504 are against a cortex 478 of a bone. The needles used in this exemplary embodiment are a bored needle 508 having a detachable tip 530 threaded with a thread 534 and a solid needle 520 with a through aperture 532 denned in its tip, for receiving detachable tip 530. Other needle types, for example as described above, may be used instead.

Figure 17B:
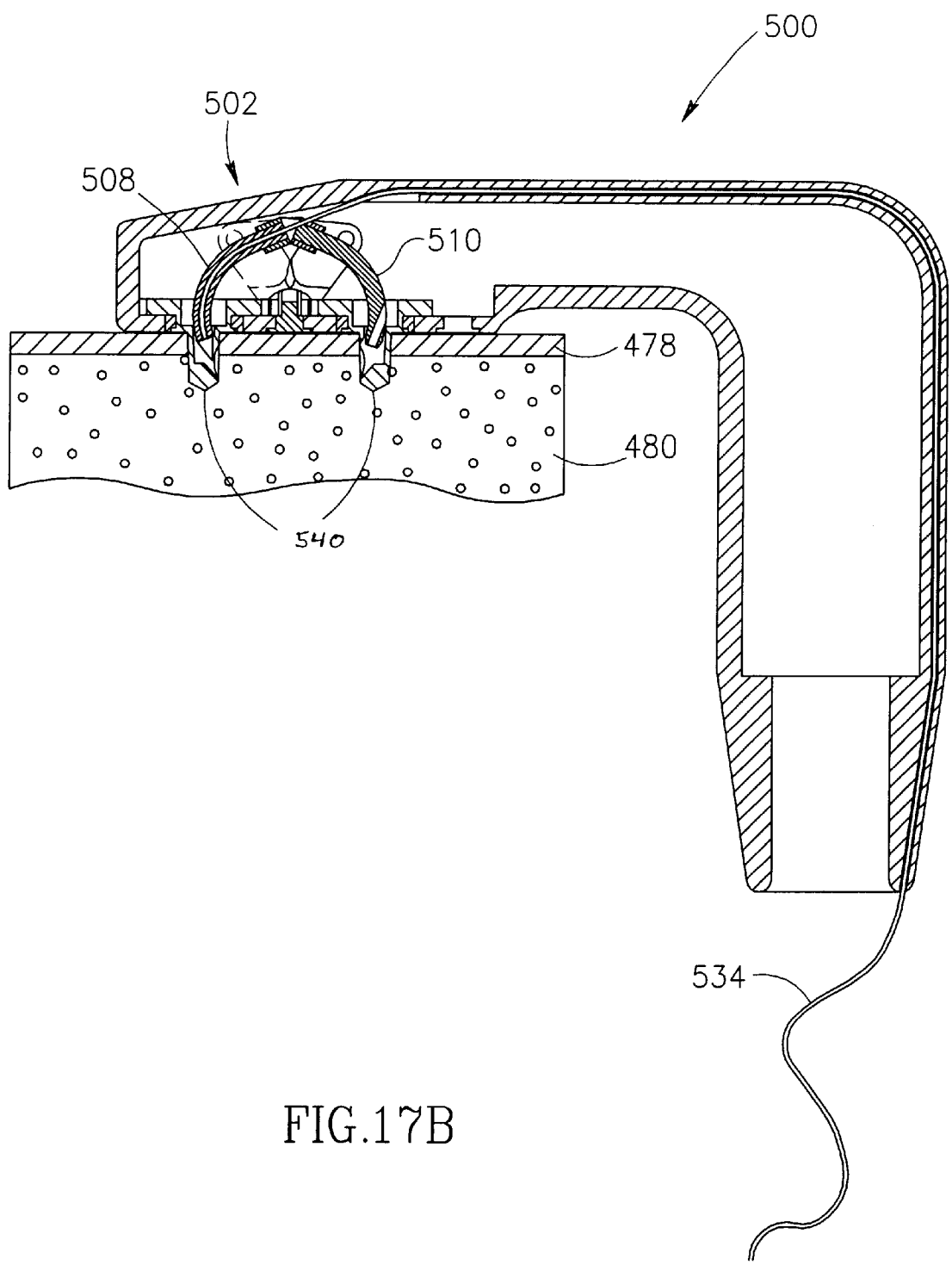

In FIG. 17B, pressure is applied to a handle (not shown) forcing drill bits 504 against cortex 478, forming a pair of cortex-bores 540, after they have rotated a sufficient amount. In a prefer embodiment of the invention, the drill bits are prevented from rotation unless a minimum pressure is applied to them, for example using a mechanical clutch. Alternatively or additionally, the number of rotations of the drill-bits is predetermined and once the number is reached the drilling stops. Once bores 540 are formed, drill bits 504 are prevented from advancing by the base of head 502, which contacts the bone or by a suitable protrusion from head 502 (not shown). The drilling depth may be set, for example by moving the protrusion axially relative to the drill bits.

Figure 17C:
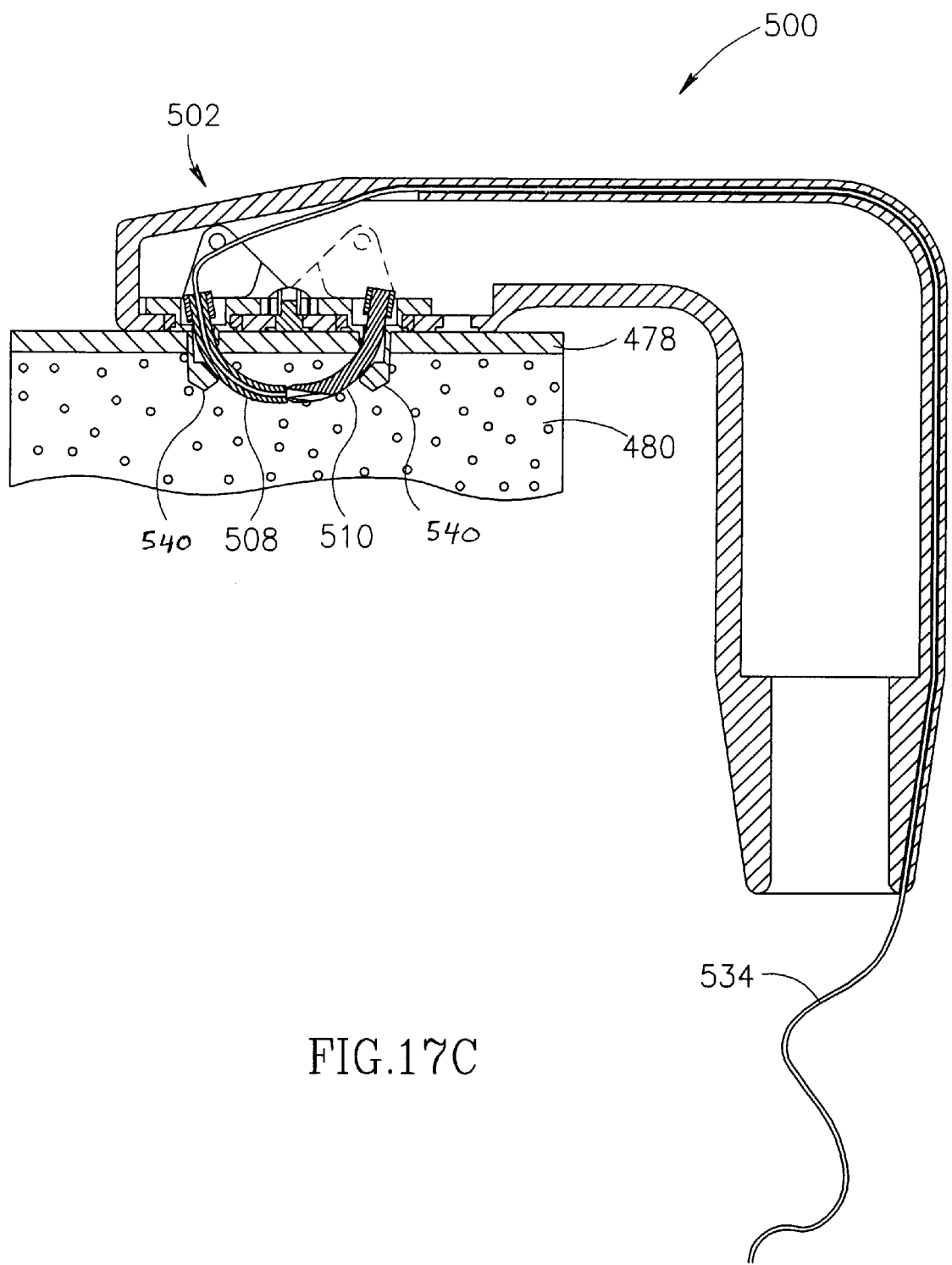

In FIG. 17C the needles are advanced so that a bore 542 is formed in medulla 480 and detachable tip 530 is engaged by aperture 532.

Figure 17D:
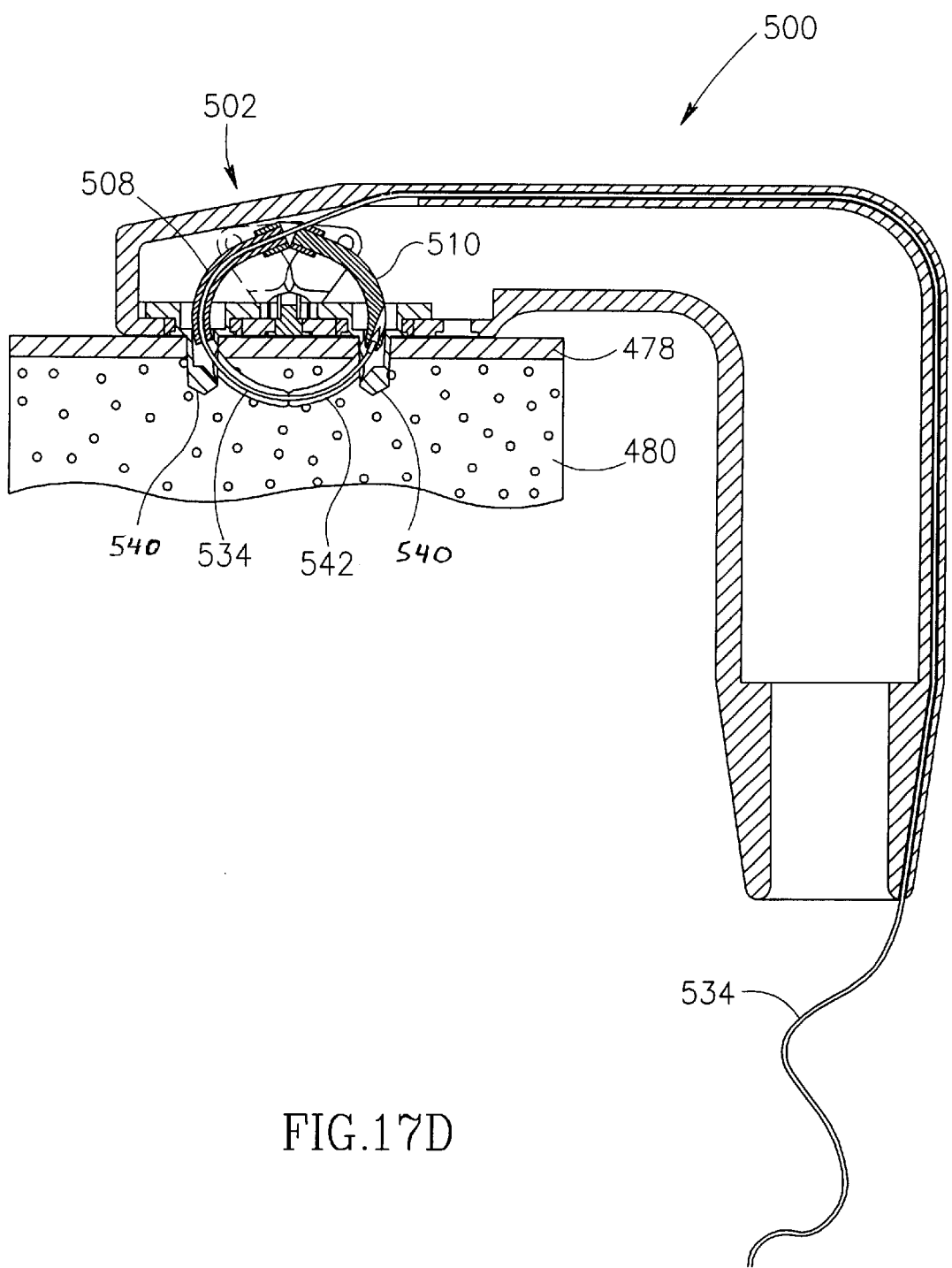

In FIG. 17D, the needles are retracted, leaving thread 534, which is attached to detachable tip 530, in bore 542.

Figure 17E:
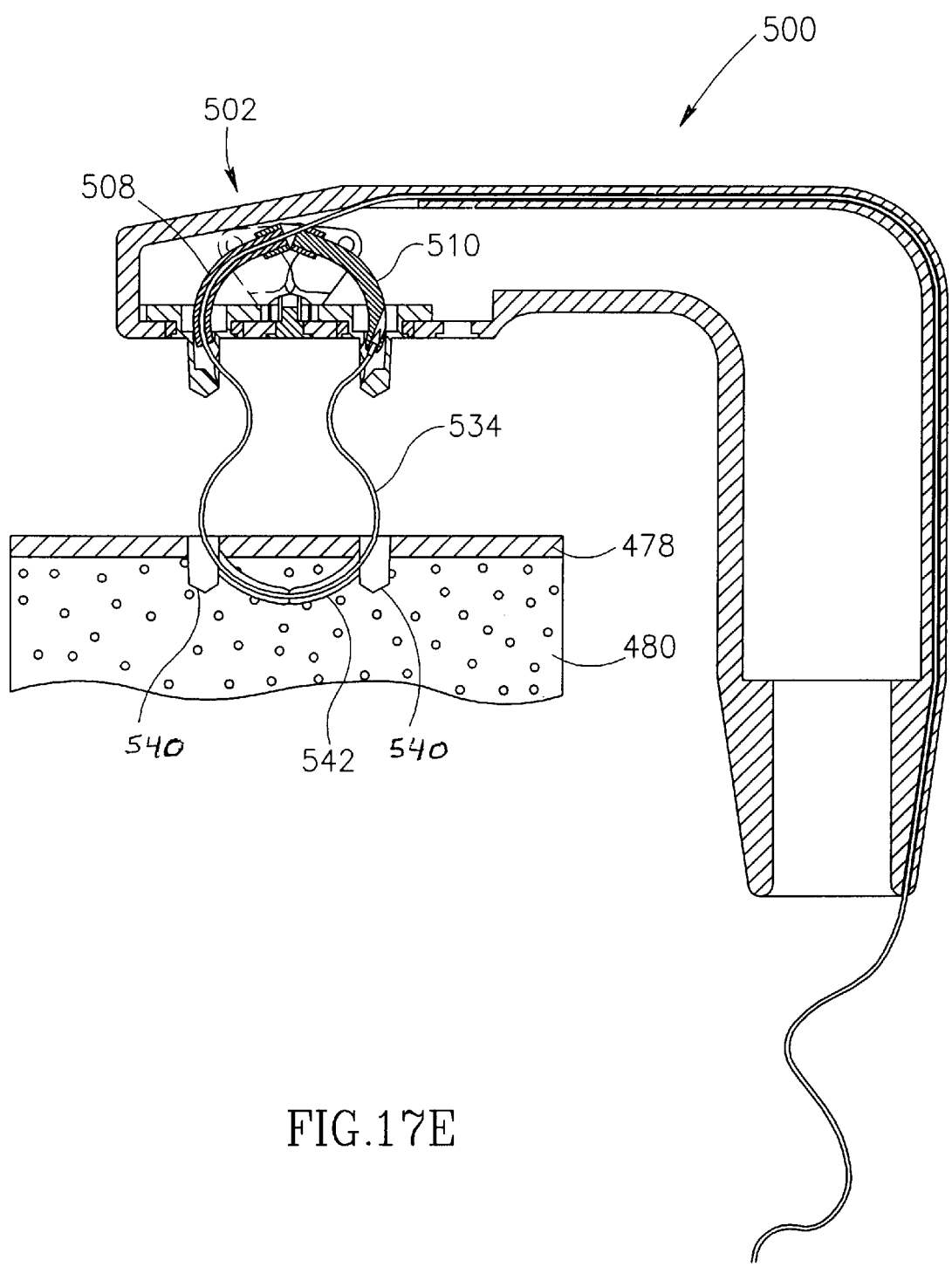

In FIG. 17E, head 502 is retracted, leaving thread 534 (or an extension of tip 530) threading the bone.

Figure 18:
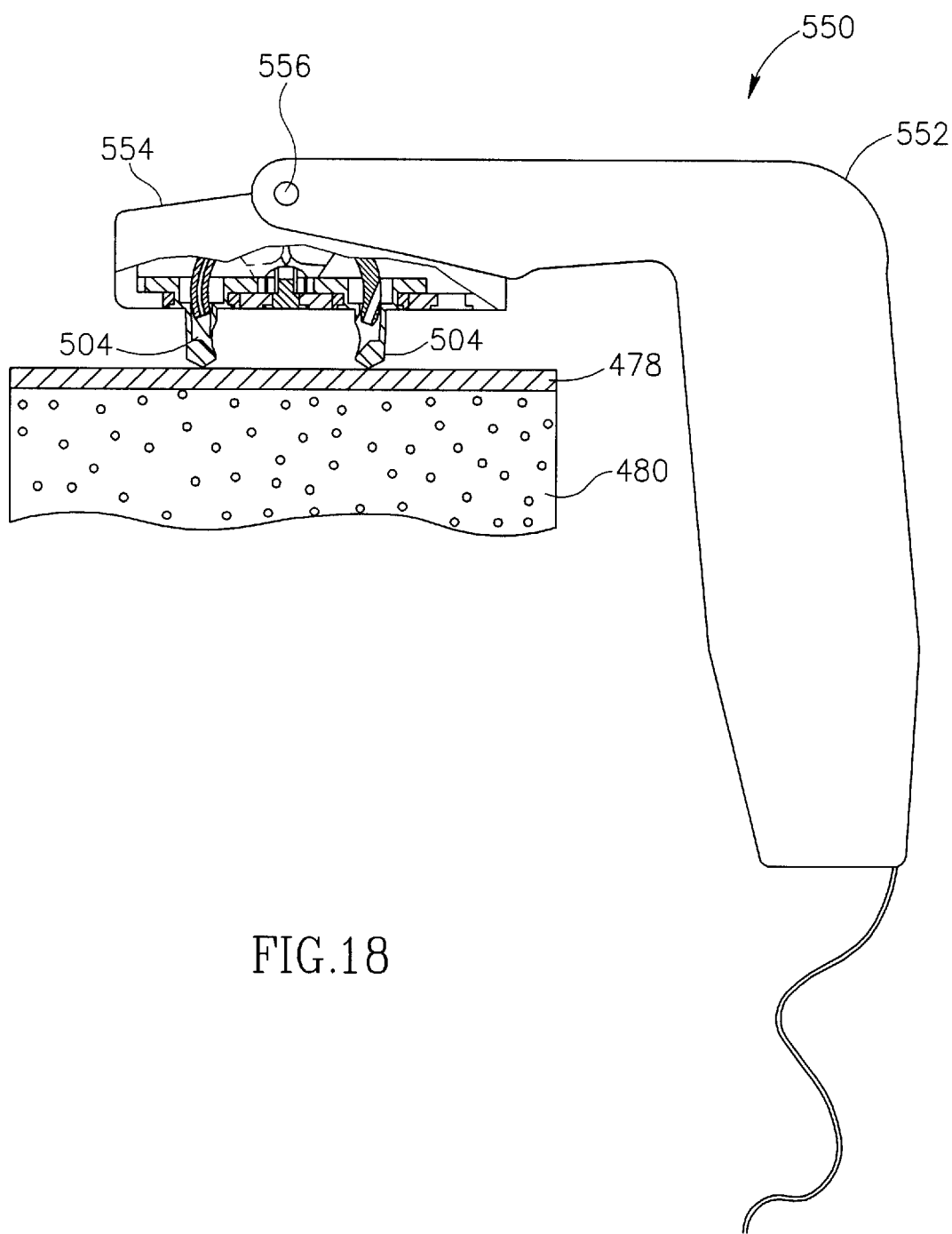
FIG. 18 illustrates a variant of the combined boring head of FIGS. 16A–B

FIG. 18 illustrates a variant 550 of device 500, which can adapt to the local bone geometry. A boring head 554 is mounted on a body 552, by a hinge 556. When head 554 is pressed against the bone, the head aligns so that both drill bits 504 contact the bone.

In all of the above figures, the thread has been shown traveling from a left needle to a right needle. It should be appreciated that this convention, as well as other conventions related to mirroring and relative placement of device elements have been adopted for simplicity of description and should not be construed to limit the preferred embodiments to those shown, for example, a thread may travel from the needle on the side of the shank to the needle on the outside of the device (unlike shown in FIG. 13A).

In a preferred embodiment of the invention, the device or parts thereof are made for one time or limited time used.

Thus, sterilization of the device can better be achieved. Further, issues of wear and maintainability are solved, allowing a cheaper device to be manufactured. In one embodiment, the device is a one-patient device and the needles are one-time use. Alternatively or additionally, the needles are one-patient use and the sutures and/or thread pusher (if provided) are one-time use. Alternatively, the device is a multi-use device and the boring head is disposable. In the example of FIG. 12A, the thread and its channel may comprise a disposable cartridge. In the example where lever 338 is not needed or is replaced by a latch pin and/or spring 342, a cartridge may comprises a plurality of pre-threaded thread pushers, which are advanced one at a time, out of a cartridge (schematically shown as 343 in FIG. 13B) into the needle bore. As one needle pusher is advanced, the next one becomes available for advancing and comes into contact with spring 342. Preferably, but not necessarily, the disposable needle pusher is provided as an extension of needle pusher 330. The size of cartridge 343 can be larger, of course, for example if a long disposable thread pusher is used. In the embodiment shown. The retraction of the needles preferably cocks spring 342.

In a preferred embodiment of the invention, even in a disposable device, the device is tested, preferably on a piece of test material (possibly an in vitro bone), after it is manufactured or prior to its being used by the physician, to insure that the device is operating properly.

The above description has focused on forming holes in a pubic bone, especially for attaching a thread through the hole for a bladder sling or a bladder or bladder neck suspension. However, a similar device may be used for other applications. In one broad class of uses, the channel is used for attaching soft tissue to a bone, using a thread that grips the bone and is engaged by the channel. Examples of attaching soft tissue include correction a dislocating shoulder (e.g., Bankard procedure), hyoid suspension, and cosmetic applications, such as tightening flabby flesh, by sing it to a bone.

Figure 19:
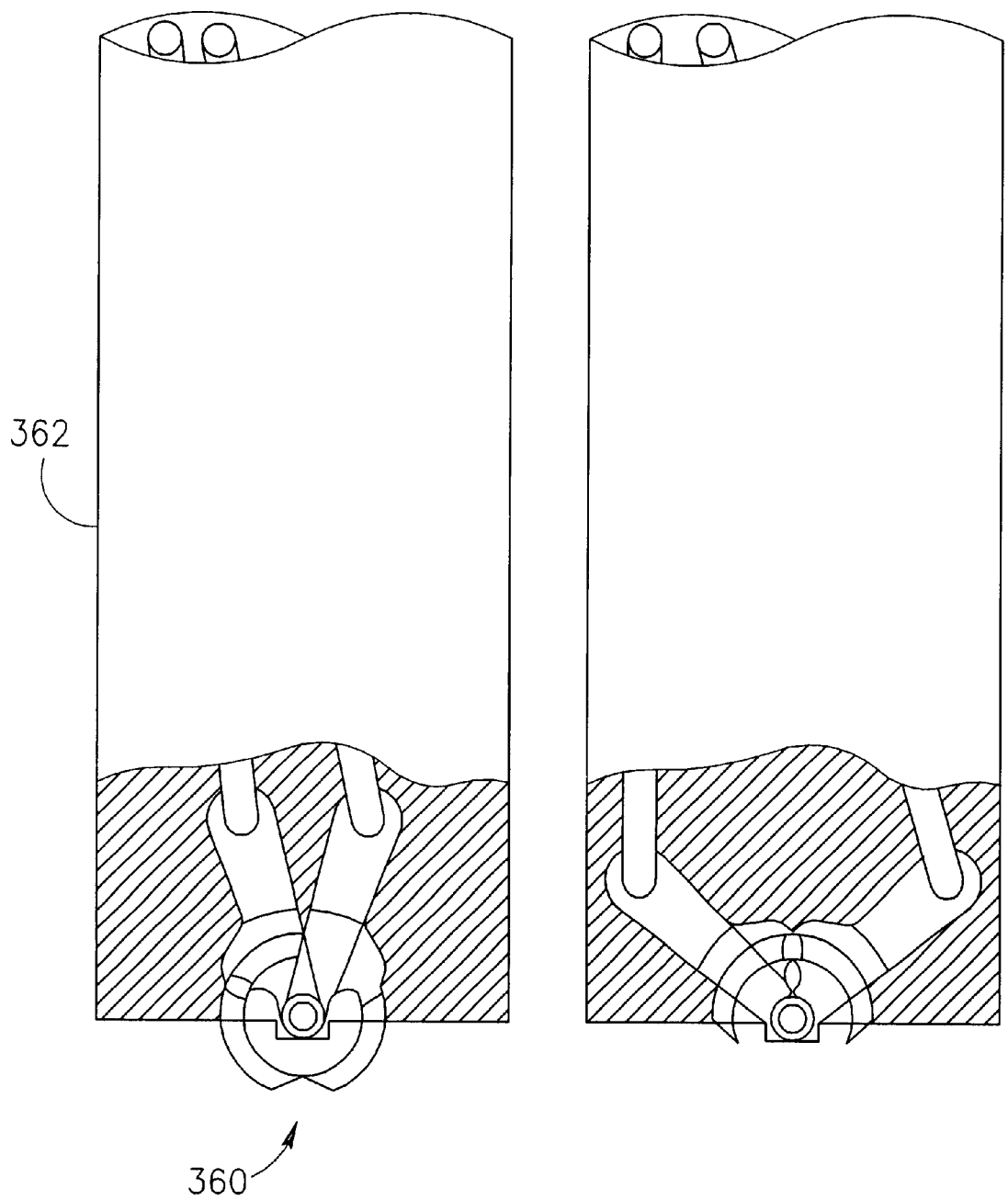
FIG. 19 illustrates a bone-boring head mounted at an end of an endoscope, catheter or trocar, in accordance with a preferred embodiment of the invention.
Figure 20:
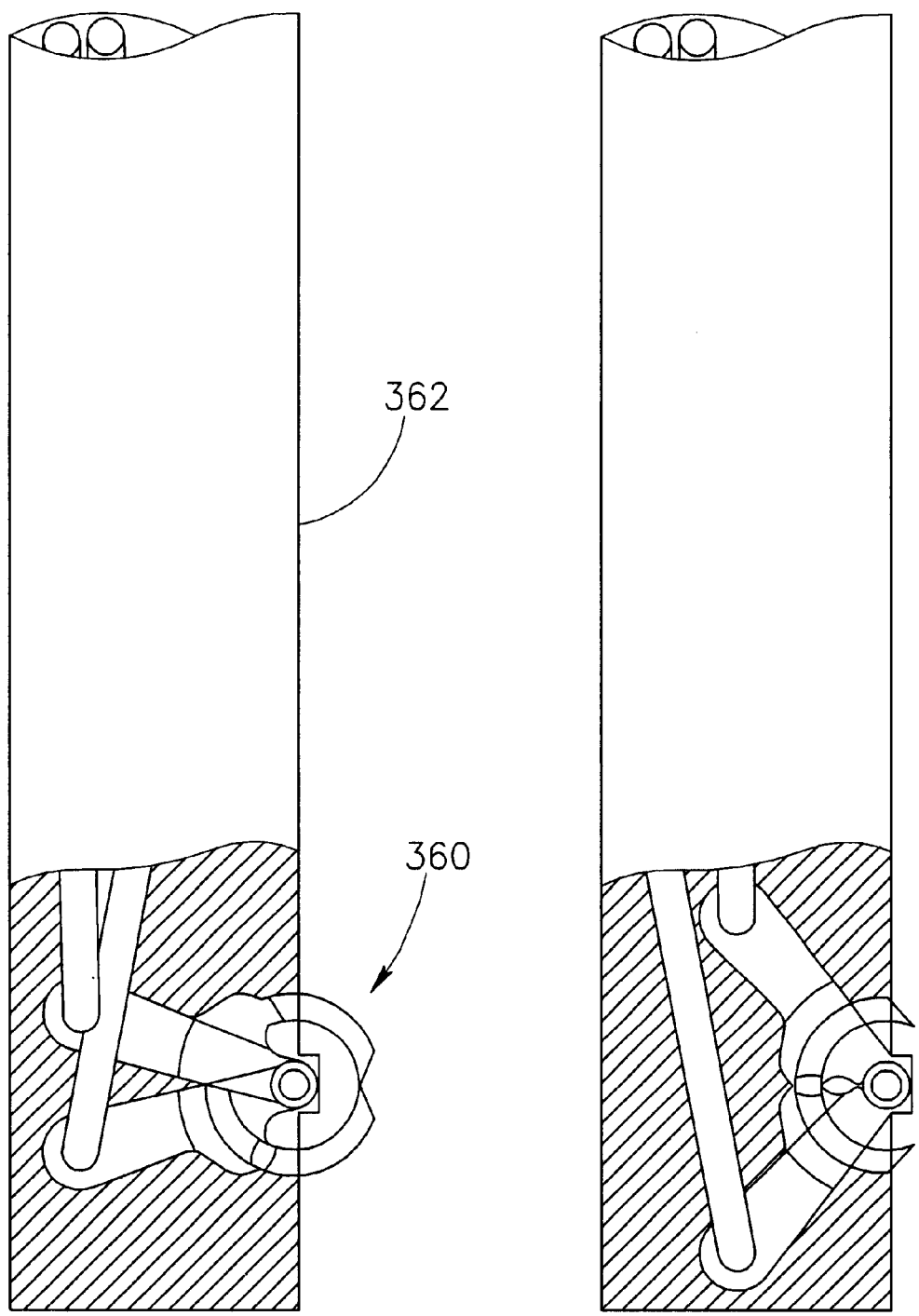
FIG. 20 illustrates a bone-boring head mounted at a side of an endoscope, catheter or trocar, in accordance with a preferred embodiment of the invention.

FIG. 19 illustrates a bone-boring head 360 mounted at an end of an endoscope, catheter or trocar 362, in accordance with a preferred embodiment of the invention. FIG. 20 illustrates bone-boring head 360 mounted at a side of endoscope, catheter or trocar 362, in accordance with a preferred embodiment of the invention. It is expected that only a small pressure is needed to maintain head 360 against a bone prior to the needles engaging the bone. In a trocar, which is substantially rigid, the pressure may be achieved by pushing against the trocar. In an endoscope, which is usually somewhat rigid, the pressure may be applied through the endoscope. In flexible endoscopes and/or flexible catheters, the pressure may be applied by advancing the endoscope and using the surrounding body tissues to apply a contra force. In some of these small-diameter devices, levers may not be suitable, due to space constraints, however, other ways of rotating the needle(s) around the hinge may be used, for example, using a screw mechanism or a motor. In some cases, a clamp or a suction nozzle (not shown) may be provided to hold head 360 against the hone. The clamp may engage bone or it may engage nearby soft tissue.

In a preferred embodiment of the invention, especially when an endoscope or tear is used for cosmetic surgery, a minimal diameter hole is formed in the body, preferably in an inconspicuous location and a boring head 360 is brought to a location where soft tissue is to be attached to bone. The suture is applied, as described herein and the thread is tied through the hole. Thereafter, the hole is sealed. This type of procedure may be especially useful for surgery of the face when implantation of staples or screws or long incisions may not be viable options.

Another class of uses is attaching implants, either using a suture, as described above or by inserting a projection of the implant into a channel formed in the bone.

Another class of uses is treating fractures of bones. In one example, small bones, such as wrist bones may be immobilized or prevented form moving apart by threading them together. Preferably, first a channel is formed in each bone and then the bones are sutured to each other (or to soft tissue, such as ligaments). Further, in cases where there are many bone fragments, such as in skull injuries or in cases of shattered jaw bones, the fragments may be stitched together. In some cases it is advantageous for the needles to oppose each other (180 degrees), possibly traveling in straight lines towards each other. Optionally, a large radius of rotation around the hinge approximates such straight lines.

Figure 21:
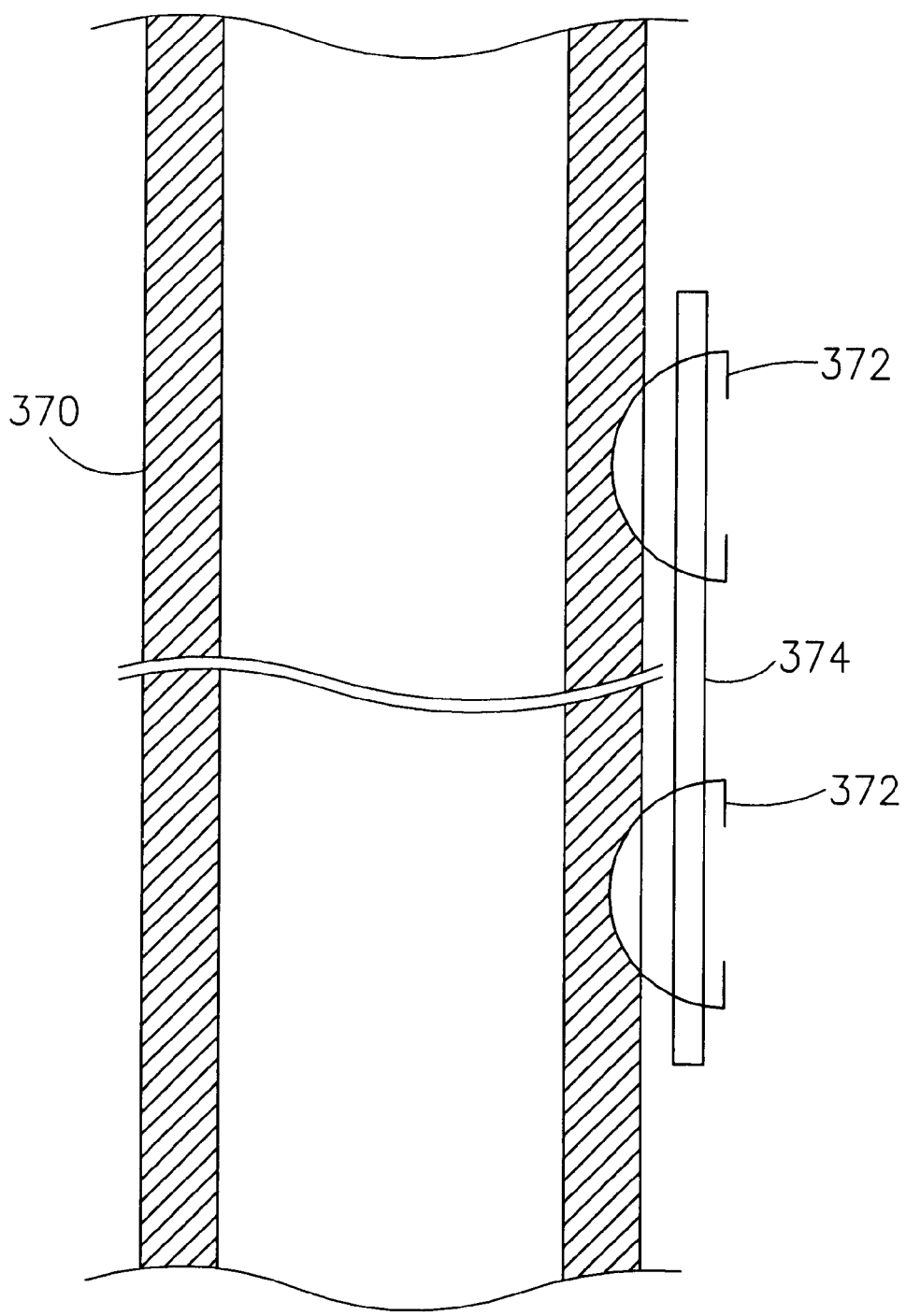
FIG. 21 illustrates a method of treating a fractured bone, in accordance with a preferred embodiment of the invention.

In a preferred embodiment of the invention, bone fragments are attached to a structural element that maintains them in place. FIG. 21 illustrates a plate 374 which is sutured to a fractured bone 370, using a plurality of sutures 372. Optionally, holes are pre-formed in the structural element for receiving the needles. Alternatively, holes in the structural element may be bored in a single step with boring the holes in the bone. Possibly, a biodegradable structural element is used, so that there is no need to remove it after the bone heals. Alternatively or additionally, the needles may be biodegradable. Another relevant procedure is sternal suturing in which a cut-open rig cage is sutured shut. In a variation of the above embodiment, plate 374 may be an intramedullar nail (possibly not filling the entire cross-section but functioning like plate 374) which is inside the bone.

The above description has focused on boring holes through bones. However, it should be noted that various aspects of the invention may be applied towards other, similar medical applications. In one example, it is noted that self-aligning and the various safety mechanisms are also useful for screw driving devices and for staplers, for example, to prevent slippage, incorrect penetration and/or inadvertent damaging of soft tissue.

With regard to staplers, the above described force transduction mechanism may be used, noting, that unlike needles, the staples remain in the body. Possibly, the staples are inserted side by side with a pair of needles, each of which needles includes a grove for receiving an arm of the staple and which needle does the actual boring. Thus, the staple itself can contain less material and/or otherwise be mechanically weaker.

Additionally, the above device may be used for tacking, which is a method where a suture or other object is attached to a bone by its being pressed between a tack and the bone. A more complete description of tacking can be found in Israel patent application number 127,978 filed Jan. 8, 1999, by applicant Influence Medical Systems Ltd., and titled "Incontinence Device", the disclosure of which is incorporated herein by reference.

Additionally, the above device can be used for implanting a bone—anchor, noting that since the hole is bored by a needle, the bone anchor can be made with less material, weaker material and/or from bio-absorbable material.

Additionally, the above-described mechanisms are useful for inserting objects into a bone at a non-perpendicular angle thereto.

It will be appreciated that the above described methods of forming a channel through bone and threading the channel and devices therefore may be varied in many ways, while remaining within the scope of the present invention. In addition, a multiplicity of various features, both of methods and of devices has been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. Also within the scope of the invention are surgical kits that include sets of bone-boring devices, bone-boring heads, needles and/or sutures. When used in the following claims, the terms "comprises", "includes", "have" and their conjugates mean, "including but not limited to".

A person skilled in the art will appreciate that the present invention is not limited by what has thus far been described. Rather, the scope of the present invention is limited only by the following claims.

What is claimed is:

1. A bone boring device, comprising:
   a hinge;
   a handle coupled to said hinge;
   at least one curved needle having a tip at one end thereof and rotatably mounted on the hinge, wherein when said tip is placed against bone and said needle is rotated on said hinge, said needle is urged into said bone; and
   said at least one curved needle having a rigidity sufficient to withstand resistance in said bone resulting from translational, non-rotational movement of said needle into said bone; and
   said at least one curved needle having a hollow bore sized to receive a suture.

2. A device according to claim 1, comprising a resting point adjacent said hinge, which resting point is adapted to be placed against said bone.

3. A device according to claim 1, wherein said curved needle has a radius of curvature matching a distance of said needle from said hinge.

4. A device according to claim 1, wherein said at least one needle comprises a first needle and a second needle.

5. A device according to claim 4, wherein said needles rotate about a same hinge for urging into said bone.

6. A device according to claim 4, wherein said needles do not share a hinge.

7. A device according to claim 4, wherein said needles are adapted to meet at their ends, when said needles are rotated around said hinge.

8. A device according to claim 7 wherein said needles are formed with a conduit therein and wherein, when said needles meet, a continuous conduit is formed along the needles.

9. A device according to claim 8 and comprising a channel substantially contiguous with said bore and adapted for advancing a thread through said channel and along said conduit.

10. A device according to claim 7, wherein said needles meet tip-to-tip.

11. A device according to claim 7, wherein said needles meet side-to-side at their ends.

12. A device according to claim 7, comprising a thread pusher for advancing thread through said bore.

13. A device according to claim 12, wherein said thread pusher extends to outside said bone boring device.

14. A device according to claim 7, wherein said first needle is adapted to engage a tip of said second needle.

15. A device according to claim 14, wherein said second needle is hollow.

16. A device according to claim 14, wherein said second needle has a grove defined along most of its length.

17. A device according to claim 14, wherein said tip comprises a detachable tip to which the thread is attached.

18. A device according to claim 17, wherein said detachable tip comprises an extension to which a thread is attached, which extension is substantially longer than said second needle.

19. A device according to claim 14, wherein said second needle is detachable from said bone boring device.

20. A device according to claim 19, wherein said needles meeting causes said second needle to detach.

21. A device according to claim 20, wherein said second needle is adapted for attaching a thread thereto.

22. A device according to claim 14, wherein said first needle defines an aperture at its tip, which aperture is adapted to engage said tip.

23. A device according to claim 22, wherein said aperture is an opening to a blind hole.

24. A device according to claim 22, wherein said aperture is an opening to a through hole.

25. A device according to claim 22, wherein said aperture connects to a hollow volume along an axis of said needle.

26. A device according to claim 25, comprising a sharp-tip mandrel that fills said hollow volume.

27. A device according to claim 26, wherein said mandrel is retracted when said needles meet.

28. A device according to claim 22, wherein said aperture connects to a hollow volume oblique to an axis of said needle.

29. A device according to claim 22, wherein said aperture is an opening to a volume extending into said needle and having a substantially constant inner diameter.

30. A device according to claim 22, wherein said aperture is an opening to a volume extending into said needle and having an inner diameter that increases away from the aperture.

31. A device according to claim 22, wherein said aperture is an opening to a slotted volume.

32. A device according to claim 1, wherein said needles and said hinge are comprised in a disposable cartridge, separable from said handle.

33. A method of boring a path in a bone, comprising:
   providing at least one curved needle having a tip and an axis;
   positioning said needle at a position adjacent the surface of said bone, such that said axis at the tip is not perpendicular to said surface; and
   advancing said needle to bore a hole into said bone.

34. A method according to claim 33, wherein boring a hole comprises boring a hole without removing bone tissue.

35. A method according to claim 33, wherein said at least one needle comprises two needles.

36. A method according to claim 33, wherein said at least one needle is a single needle.

* * * * *